United States Patent
Yamamoto et al.

(10) Patent No.: US 7,219,708 B2
(45) Date of Patent: May 22, 2007

(54) APPARATUS AND METHOD FOR INSPECTING FILM CARRIER TAPE FOR MOUNTING ELECTRONIC COMPONENT

(75) Inventors: Masahiko Yamamoto, Shimonoseki (JP); Hideaki Kaneko, Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 0 days.

(21) Appl. No.: 10/783,114

(22) Filed: Feb. 20, 2004

(65) Prior Publication Data
US 2004/0163482 A1    Aug. 26, 2004

(30) Foreign Application Priority Data
Feb. 21, 2003  (JP)  ............................. 2003-044430

(51) Int. Cl.
B32B 41/00  (2006.01)
B65H 26/04  (2006.01)

(52) U.S. Cl. .................. 156/361; 156/378; 156/379

(58) Field of Classification Search ................ 156/259, 156/271, 361, 378, 379; 73/865.8; 83/73
See application file for complete search history.

(56) References Cited

FOREIGN PATENT DOCUMENTS

| JP | 09-092692 A | 4/1997 |
|---|---|---|
| JP | 10-256278 A | 9/1998 |
| JP | 2000-182061 A | 6/2000 |
| JP | 2000-227401 A | 8/2000 |
| JP | 2001-035891 A | 2/2001 |
| JP | 2001-345345 | * 12/2001 |
| JP | 2003-332392 A | 11/2003 |

OTHER PUBLICATIONS

Translation of JP 2001-035891 (Japanese reference submitted with Jun. 7, 2004 IDS).*

* cited by examiner

*Primary Examiner*—George Koch
(74) *Attorney, Agent, or Firm*—The Webb Law Firm

(57) ABSTRACT

An apparatus and method for inspecting a film carrier tape for mounting electronic component, in which film carrier tapes for mounting electronic component provided with a plurality of electronic component mounting portions in multiple strips in a transverse direction are exactly used and which can be inspected simultaneously, so that inspection efficiency can be greatly enhanced. Furthermore, the film carrier tapes for mounting electronic component are separated into individual strips after inspection and can be taken up on individual reels without a winding shift. A film carrier tape for mounting electronic component in multiple strips which are unwound from an unwinding device, is cut into individual film carrier tapes for mounting electronic component in stripes strips by a slit device, then caused to run in parallel with each other and simultaneously inspected in an inspecting section, then they are simultaneously taken up on a plurality of take-up reels attached to an identical take-up shaft of a take-up device in parallel with each other, respectively.

20 Claims, 13 Drawing Sheets

APPARATUS AND METHOD FOR INSPECTING FILM CARRIER TAPE FOR MOUNTING ELECTRONIC COMPONENT

BACKGROUND OF THE INVENTION

1. Field of the Invention

The present invention relates to an apparatus and method for inspecting a film carrier tape for mounting electronic component which finally inspects the defect of an appearance before shipment of a film carrier tape for mounting electronic component (TAB (Tape Automated Bonding) tape, a T-BGA (Tape Ball Grid Array) tape, a CSP (Chip Size Package) tape, an ASIC (Application Specific Integrated Circuit) tape, a COF (Chip on Film) tape, a 2 metal (double-sided wiring) tape, a tape for multilayer wiring and the like) (which will be hereinafter referred to as a "film carrier tape for mounting electronic component) and then displays the defect of a product on a defective product through punching or the like, for example.

2. Description of the Related Art

Although a demand for a printed wiring board for mounting an electronic component such as an IC (an integrated circuit) or an LSI (a large scale integrated circuit) has rapidly been increased with the development of an electronics industry, a reduction in a size and a weight and an enhancement in a function of an electronic apparatus have been required. For a method for mounting these electronic components, recently, a mounting method using film carrier tapes for mounting electronic component such as a TAB tape, a T-BGA tape and an ASIC tape has been employed. In particular, an importance has been increased in an electronic industry using a liquid crystal display (LCD) in which an enhancement in fineness, a reduction in a thickness and a decrease in the area of the frame of a liquid crystal screen are demanded, for example, a personal computer.

In such a film carrier tape for mounting electronic component, quality thereof has been inspected. Conventionally, there has been executed an inspecting method for carrying out a visual inspection to be a human visual inspection (a transmitted light inspection or a reflected light inspection) and displaying a defect for a defective product through punching, inking, dry ink or the like as a result of various quality inspections of a disconnection, a short circuit, a dent (i.e. reducing portion of wiring lead width), a projection and furthermore a pattern defect thereof, a plating defect, a deformation of the shape of the tape, and a defect of solder resist and the like.

For this reason, there has conventionally been proposed an inspecting apparatus in which a film carrier tape for mounting electronic component in one strip provided with one or more electronic component mounting portion in a transverse direction is unwound out of an unwinding device. Further, in the conventional inspecting apparatus, a predetermined inspection in an inspecting section is carried out and the same tape is taken up by a take-up device (for example, see Japanese Laid-Open Patent Publication No. 2001-35891, Japanese Laid-Open Patent Publication No. 2000-227401, Japanese Laid-Open Patent Publication No. 2000-182061, Japanese Laid-Open Patent Publication No. 10-256278 and Japanese Laid-Open Patent Publication No. 9-92692).

More specifically, as shown in FIG. 13, in a conventional inspecting apparatus 100, a film carrier tape 102 for mounting electronic component in one strip, which is provided with one or more electronic component mounting portion in a transverse direction, is wound upon an unwinding reel 104. The unwinding reel 104 is attached to an unwinding shaft 108 of an unwinding device 106, so that the film carrier tape 102 for mounting electronic component is unwound out of the unwinding device 106.

The film carrier tape 102 for mounting electronic component which is unwound out of the unwinding device 106, is subjected to a visual inspection in an inspecting section 110, for example. Then, if a defective portion is present, a defect is displayed by a defect display device 112 such as punching.

After the visual inspection and the defect displaying step are ended, thus, the film carrier tape 102 for mounting electronic component is wound upon a take-up reel 118 attached to a take-up shaft 116 of a take-up device 114.

In the method in which the film carrier tape 102 for mounting electronic component in one strip is unwound out of the unwinding device 106 and in which the predetermined inspection in the inspecting section 110 is carried out and in which the film carrier tape 102 is taken up by means of the take-up device 114, however, the inspection is carried out in every strip in the inspecting section 110.

As a result, the film carrier tape 102 for mounting electronic component, which can be inspected one at a time, is the film carrier tape wound upon one reel. Under the existing circumstances in which a mass production is required, therefore, an inspection efficiency is still more insufficient.

In a method for manufacturing a film carrier tape for mounting electronic component, moreover, a film carrier tape for mounting electronic component, which is provided with a plurality of electronic component mounting portions in multiple strips in a transverse direction (so-called "multiple take-up"), has recently been manufactured in order to enhance productivity.

When such a film carrier tape for mounting electronic component in multiple strips is to be inspected, a slit step of previously cutting the film carrier tape into individual film carrier tapes for mounting electronic component in strips is carried out by using a slit device and an inspection is executed every strip for the film carrier tape thus slit.

More specifically, a warpage is generated in the transverse direction of the film carrier tape for mounting electronic component in multiple strips. For this reason, an accurate inspection cannot be carried out. Moreover, when the film carrier tapes for mounting electronic component in multiple strips are slit after a visual inspection, it is necessary to carry out again an inspection for an inner lead bend, a flaw, a foreign matter and the like. Furthermore, the slit step is carried out before the inspection due to the restrictions on the equipment of a user. The inspection is executed of every strip for the slit film carrier tape.

SUMMARY OF THE INVENTION

In consideration of the existing circumstances, it is an object of the present invention to provide an apparatus and method for inspecting a film carrier tape for mounting electronic component, in which a plurality of electronic component mounting portions is provided in multiple strips in a transverse direction and which is slit into each strip and which can be inspected at the same time, so that an inspection efficiency can be greatly enhanced, and furthermore, the film carrier tape for mounting electronic component in each strip can be taken upon each reel without a winding shift after the inspection.

In order to solve the problems of the conventional art and to attain the object described above, the present invention provides an apparatus for inspecting a film carrier tape for mounting electronic component in which a plurality of electronic component mounting portions is provided in multiple strips in a transverse direction, comprising:

an unwinding device for unwinding the film carrier tape for mounting electronic component in the multiple strips in which the individual film carrier tapes for mounting electronic component previously cut and separated into the individual strips are wound upon an unwinding reel, respectively;

an inspecting section for simultaneously inspecting the film carrier tapes for mounting electronic component, which are cut into strips, while causing them to run in parallel with each other; and a take-up device for simultaneously taking up the film carrier tapes for mounting electronic component cut into strips, which are inspected in the inspecting section, upon a plurality of take-up reels attached to an identical take-up shaft in parallel, respectively.

Moreover, the present invention provides a method for inspecting a film carrier tape for mounting electronic component in which a plurality of electronic component mounting portions is provided in multiple strips in a transverse direction, comprising the steps of:

unwinding, from an unwinding device, the film carrier tape for mounting electronic component in the multiple strips in which the individual film carrier tapes for mounting electronic component previously cut and separated into strips are wound upon an unwinding reel, respectively;

simultaneously inspecting the film carrier tapes for mounting electronic component, which are cut into strips, in an inspecting section while causing them to run in parallel with each other; and simultaneously taking up the film carrier tapes for mounting electronic component cut into strips, which are inspected in the inspecting section, upon a plurality of take-up reels attached to an identical take-up shaft of a take-up device in parallel, respectively.

By such a structure, the film carrier tapes for mounting electronic component, which are previously cut into individual strips, are unwound from the unwinding reel of the unwinding device respectively, and the film carrier tapes run in parallel with each other and pass through the inspecting section in the cutting state in the individual strips without mutually causing a positional shift.

Accordingly, the film carrier tapes for mounting electronic component in plural strips running in parallel can be subjected to a visual inspection to be a visual inspection (a transmitted light inspection and a reflected light inspection) simultaneously and accurately in the inspecting section. As a result of various quality inspections for a disconnection, a short circuit, a dent (i.e., reducing portion of wiring lead width), a projection and the like, a defect display can be carried out over a defective product through punching, inking, dry ink or the like.

Therefore, the film carrier tapes for mounting electronic component, which are provided with a plurality of electronic component mounting portions in multiple strips in the transverse direction, can be exactly used and inspected at a time. Thus, an inspection efficiency and inspection precision can be enhanced very greatly.

In addition, it is possible to mutually separate the individual film carrier tapes for mounting electronic component in the strips without mutually causing a positional shift and to take up the individual film carrier tapes upon the individual reels without a winding shift after the inspection.

More specifically, according to the present invention, an inspection processing can be carried out continuously and accurately in large quantities, a processing efficiency can be enhanced very greatly. Furthermore, the processing can be carried out by one operator so that a cost can be reduced.

Furthermore, the present invention provides an apparatus for inspecting a film carrier tape for mounting electronic component in which a plurality of electronic component mounting portions is provided in multiple strips in a transverse direction, comprising:

an unwinding device for unwinding the film carrier tapes for mounting electronic component in the multiple strips which are wound upon an unwinding reel;

a slit device for cutting the film carrier tapes for mounting electronic component in the multiple strips, which are unwound from the unwinding device, into individual film carrier tapes for mounting electronic component in strips;

an inspecting section, for causing the film carrier tapes for mounting electronic component, which are cut into strips by the slit device, to run in parallel with each other and simultaneously inspecting them; and a take-up device for simultaneously taking up the film carrier tapes for mounting electronic component cut into strips, which are inspected in the inspecting section, upon a plurality of take-up reels attached to an identical take-up shaft in parallel, respectively.

Moreover, the present invention provides a method for inspecting a film carrier tape for mounting electronic component in which a plurality of electronic component mounting portions is provided in multiple strips in a transverse direction, comprising the steps of:

unwinding, from an unwinding device, the film carrier tape for mounting electronic component in the multiple strips which are wound upon an unwinding reel;

cutting the film carrier tapes for mounting electronic component in the multiple strips, which are unwound from the unwinding device, into individual film carrier tapes for mounting electronic component in strips by a slit device;

causing the film carrier tapes for mounting electronic component, which are cut into strips by the slit device, to run in parallel with each other and simultaneously inspecting them in an inspecting section; and simultaneously taking up the film carrier tapes for mounting electronic component cut into strips, which are inspected in the inspecting section, upon a plurality of take-up reels attached to an identical take-up shaft of a take-up device, respectively.

By such a structure, the film carrier tapes for mounting electronic component, which are provided with a plurality of electronic component mounting portions in multiple strips in the transverse direction, are used without cutting and separating and unwound from the unwinding device, and are exactly cut into individual film carrier tapes for mounting electronic section in strips by means of the slit device.

The individual film carrier tapes for mounting electronic component in strips thus obtained by the cutting run in parallel with each other and pass through the inspecting section without mutually causing a positional shift.

Accordingly, the film carrier tapes for mounting electronic component in the plural strips, which run in parallel, can be subjected to a visual inspection to be an visual inspection (a transmitted light inspection and a reflected light inspection) simultaneously and accurately in the inspecting section. As a result of various quality inspections for a disconnection, a short circuit, a dent (i.e., reducing portion of wiring lead width), a projection and the like, a defect display can be carried out over a defective product through punching, inking, dry ink or the like.

Therefore, the film carrier tapes for mounting electronic component, which are provided with a plurality of electronic component mounting portions in multiple strips in the transverse direction, can be used and inspected simultaneously. Thus, an inspection efficiency and inspection precision can be enhanced very greatly.

In addition, it is possible to mutually separate the individual film carrier tapes for mounting electronic component in strips without mutually causing a positional shift and to take up the individual film carrier tapes upon the individual reels without a winding shift after the inspection.

More specifically, according to the present invention, an inspection processing can be carried out continuously and accurately in large quantities, a processing efficiency can be enhanced very greatly, and furthermore, the processing can be carried out by one operator so that a cost can be reduced.

According to the present invention, in these cases, the film carrier tapes for mounting electronic component, which are cut into strips and are inspected in the inspecting section, can also be simultaneously taken upon a plurality of take-up reels attached to the separate take-up shafts of the take-up device in parallel, respectively.

Consequently, the tapes can be separately taken upon the reels of the separate take-up shafts. As a result, the tapes can be transferred separately to the next steps, which is convenient.

Furthermore, the present invention is characterized in that the inspecting section includes a guide member for causing film carrier tapes for mounting electronic component, which are cut into strips, to run in parallel with each other, the guide member comprising:

a side guide portion on both ends which serves to guide both end side portions of the film carrier tape for mounting electronic component on an outermost side; and an adjacent part guide portion which is protruded to guide adjacent side portions of the film carrier tapes for mounting electronic component cut into strips between the guide portions on the both ends.

By such a structure, all the adjacent side portions and the side portions on the both ends of the film carrier tapes for mounting electronic component, which are cut into strips, are supported and guided by the side guide portion and the adjacent part guide portion in the guide member.

In the inspecting section, accordingly, the film carrier tapes for mounting electronic component, which are caused to run in parallel, are not curved in the transverse direction, that is, are not flexed respectively. Consequently, inspecting positions are flat and constant. As a result, it is possible to carry out an accurate quality inspection with high precision without shifting the focal point of a magnifying glass or the like, in the quality inspection requiring very high precision for an inner lead bend, a flaw and the like.

Moreover, the present invention is characterized by a drive gear for conveying the film carrier tapes for mounting electronic component, which are unwound from the unwinding device and cut into strips by the slit device, while causing them to run in parallel with each other, the drive gear including:

a both end gear mated with a sprocket hole in side portions on both ends of the film carrier tape for mounting electronic component on the outermost side; and an intermediate gear mated with a sprocket hole provided in the adjacent side portions of the film carrier tape for mounting electronic component cut into strips between the both end gears.

By such a structure, all of the sprocket holes provided in the adjacent side portions and the side portions on the both ends of the film carrier tapes for mounting electronic component, which are cut into strips, are mated with the both end gears and the intermediate gear in the drive gear, and they are simultaneously conveyed at an equal speed.

In the inspecting section, accordingly, the positions of the film carrier tapes for mounting electronic component which are caused to run in parallel are not shifted from each other. Therefore, it is possible to simultaneously carry out an accurate quality inspection with high precision for a plurality of film carrier tapes for mounting electronic component.

Furthermore, the present invention is characterized by a guide roller, the guide roller including:

a side guide protruded portion on both ends which serves to guide both end side portions of the film carrier tape for mounting electronic component on an outermost side; and an adjacent part guide protruded portion protruded to separate and guide adjacent side portions of the film carrier tapes for mounting electronic component cut into strips between the side guide protruded portions on the both ends.

By such a structure, the adjacent side portions of the film carrier tapes for mounting electronic component, which are cut into strips, are guided in a mutual separating state by the adjacent part guide protruded portion in the guide roller.

In the conveyance, therefore, the adjacent side portions of the film carrier tapes for mounting electronic component can be prevented from coming in contact with each other and being worn away and damaged. Consequently, quality can be enhanced and a winding shift or the like can be prevented from being caused in the take-up.

Moreover, the present invention is characterized in that a plurality of take-up reels, which are attached to the identical take-up shaft of the take-up device in parallel with each other, are fixed into through holes provided in the vicinity of centers of the reels by means of removable engaging bar members.

By such a structure, the take-up reels, which are attached to the identical take-up shaft of the take-up device in parallel with each other, are fixed to each other by means of the engaging bar members inserted in the through holes provided in the vicinity of the centers of the reels.

Accordingly, the take-up reels are not shifted from each other in the take-up so that the take-up is carried out at an equal speed in the same take-up way. Consequently, it is possible to simultaneously obtain a film carrier tape for mounting electronic component in the same winding form without generating a winding shift.

Furthermore, the present invention is characterized in that the identical take-up shaft of the take-up device is constituted by an air shaft capable of expanding to increase a diameter thereof upon receipt of supply of air, and a plurality of take-up reels attached to the take-up shaft in parallel with each other is thus fixed to each other.

By such a structure, the air is supplied to the air shaft constituting the take-up shaft. Consequently, the shaft is expanded and increased in a diameter so that a plurality of take-up reels, which are attached to the identical take-up shaft of the take-up device in parallel with each other, are fixed to each other.

Accordingly, the take-up reels are not shifted from each other in the take-up so that the take-up is carried out at an equal speed in the same take-up way. Consequently, it is possible to simultaneously obtain a film carrier tape for mounting electronic component in the same winding form without generating a winding shift.

In addition, in this case, it is possible to control the attachment, removal and fixation of the take-up reel, a fixing force and a winding unevenness by regulating the supply and release of air and an air pressure. Consequently a very great convenience can be obtained and a complicated work is not required.

Moreover, the present invention is characterized in that the inspecting section includes a magnifying lens device for magnifying the film carrier tape for mounting electronic component in order to carry out an inspection, the magnifying lens device including a magnifying lens for magnifying, in a total width direction, the film carrier tapes for mounting electronic component which are cut into strips and running in parallel with each other.

By such a structure, the film carrier tape for mounting electronic component in the total width direction can be enlarged through the magnifying lens. Consequently, it is possible to simultaneously carry out an accurate quality inspection with high precision for a plurality of film carrier tapes for mounting electronic component.

Furthermore, the present invention is characterized in that the magnifying lens device has a magnification of 1.4 or more at an enlargement ratio of a length.

More specifically, if the magnification of the magnifying lens device is set within this range, the defect of the film carrier tape for mounting electronic component can be detected sufficiently.

Moreover, the present invention is characterized in that separate dancer rollers are provided for the film carrier tapes for mounting electronic component, which are cut into strips, between the unwinding device and the inspecting section, respectively.

Furthermore, the present invention is characterized in that separate dancer rollers are provided for the film carrier tapes for mounting electronic component, which are cut into strips, between the take-up device and the inspecting section, respectively.

The separate dancer rollers are provided for the film carrier tapes for mounting electronic component, which are cut into strips, between the unwinding device and the inspecting section and between the take-up device and the inspecting section, respectively. By these dancer rollers, therefore, it is possible to separately regulate the amounts of looseness of the film carrier tapes for mounting electronic component, thereby smoothly carrying out unwinding and take-up.

Moreover, the present invention is characterized in that an identical dancer roller is provided for the film carrier tapes for mounting electronic component, which are cut into strips, between the unwinding device and the inspecting section.

Furthermore, the present invention is characterized in that an identical dancer roller is provided for the film carrier tapes for mounting electronic component, which are cut into strips, between the take-up device and the inspecting section.

By such a structure, it is possible to regulate the amounts of looseness of the film carrier tapes for mounting electronic component to smoothly carry out the unwinding and the take-up by simply controlling the identical dancer roller between the unwinding device and the inspecting section and between the take-up device and the inspecting section.

Moreover, the present invention is characterized by a looseness control device for detecting a position of the dancer roller to control an amount of looseness of the film carrier tape for mounting electronic component.

Consequently, it is possible to regulate the amount of the looseness of the film carrier tape for mounting electronic component, thereby smoothly carrying out the unwinding and the take-up.

Furthermore, the present invention is characterized in that the looseness control device includes a guide member for separately changing a guide path for the film carrier tape for mounting electronic component in each strip which is to be guided by the dancer roller.

Thus, when the film carrier tapes for mounting electronic component, which are cut into strips, are unwound and taken up by means of the identical dancer roller, for example, they are unwound and taken up for the strips and the dancer roller is inclined due to a slight difference in a unwound speed and a take-up speed, and therefore, the amount of the looseness cannot be controlled smoothly so that the film carrier tapes for mounting electronic component come in contact with each other and are thus worn away and damaged. By separately changing the guide path for each strip by means of the guide member, however, the amount of the looseness can be set to be equal. Therefore, such a situation can be prevented effectively.

DETAILED DESCRIPTION OF THE INVENTION

An embodiment (example) of the present invention will be described below in more detail with reference to the drawings.

Figure 1:
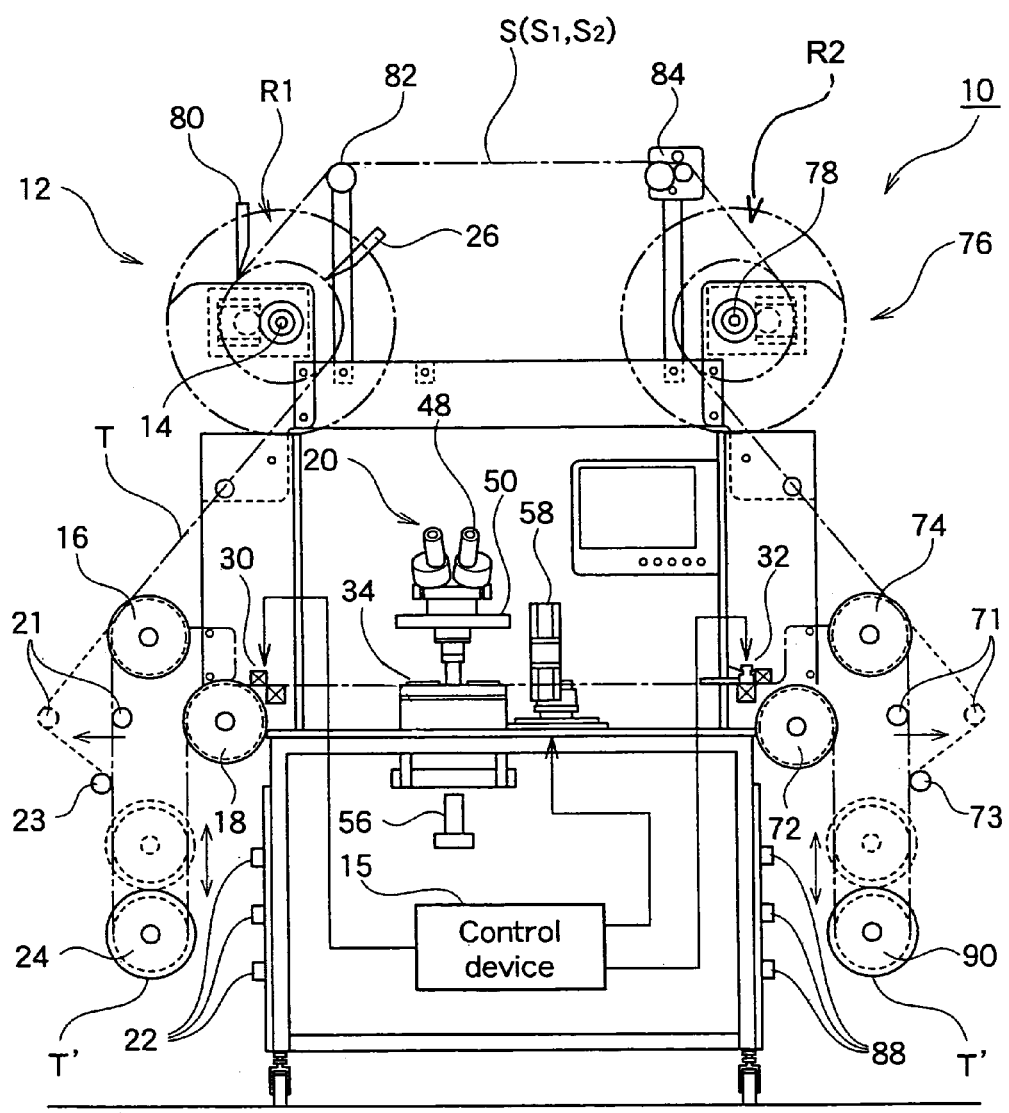
FIG. 1 is a front view showing an apparatus for inspecting a film carrier tape for mounting electronic component according to an embodiment of the present invention.
Figure 2:
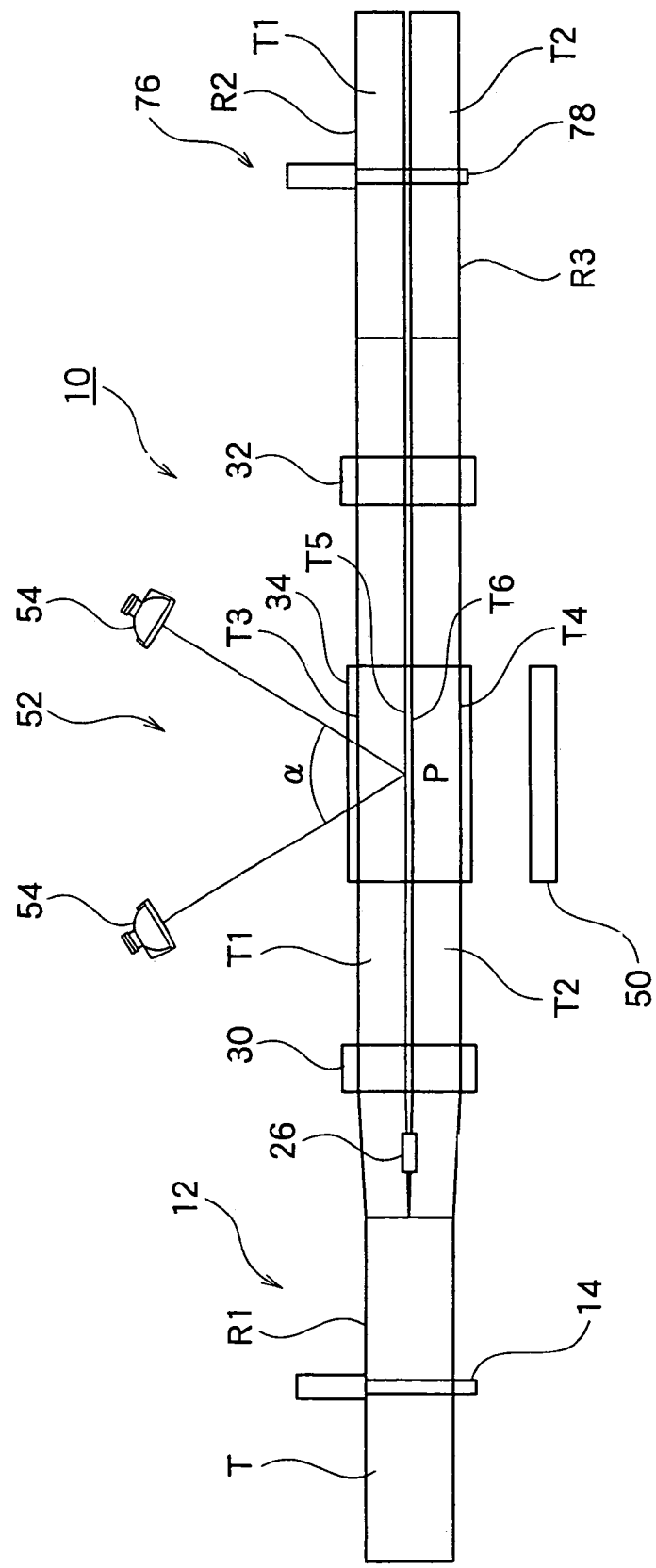
FIG. 2 is a schematic view for explaining a method for inspecting a film carrier tape for mounting electronic component according to the present invention.
Figure 3:
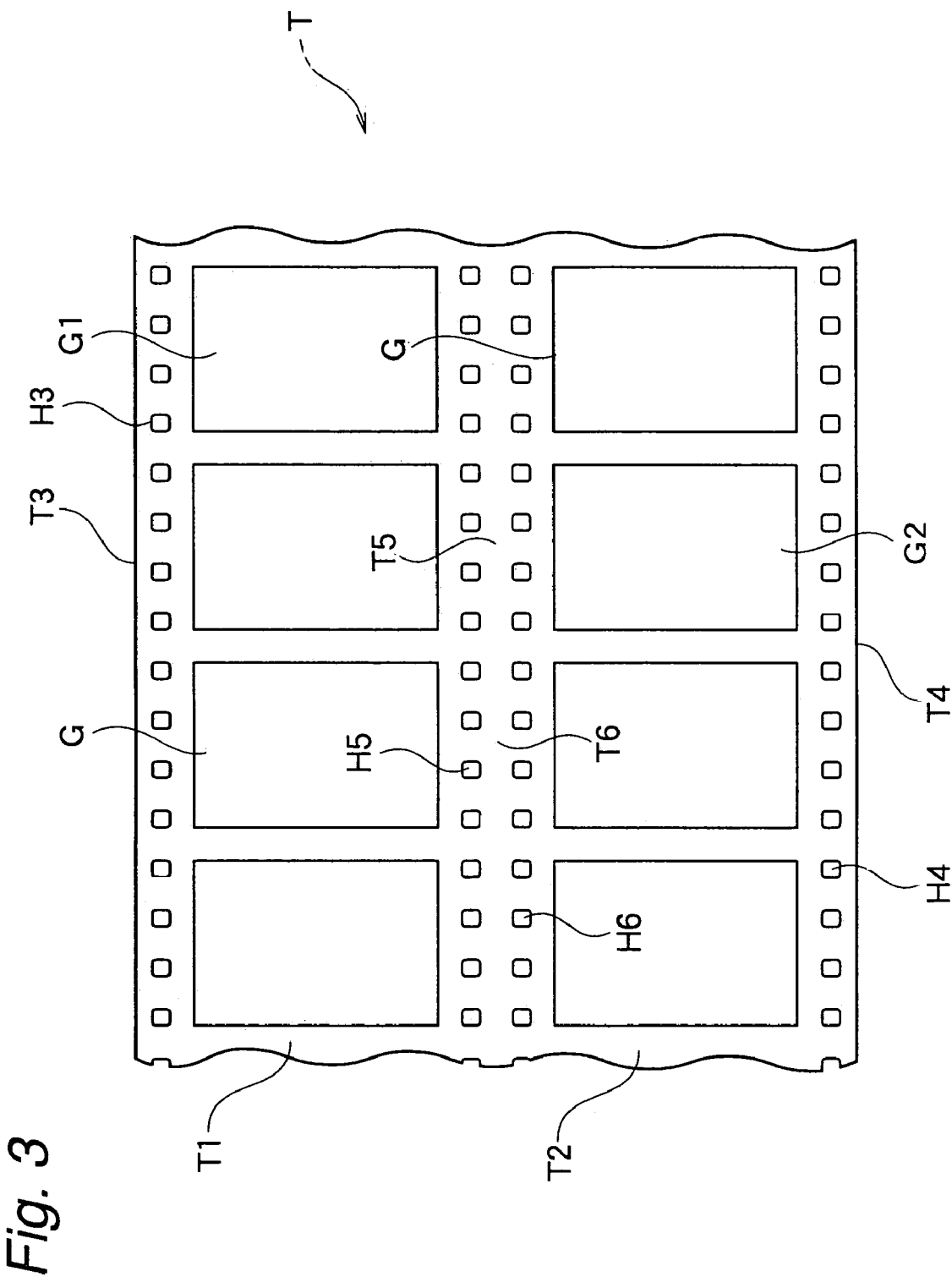
FIG. 3 is a top view showing a film carrier tape for mounting electronic component which is used in the apparatus for inspecting a film carrier tape for mounting electronic component according to the present invention.
Figure 4:
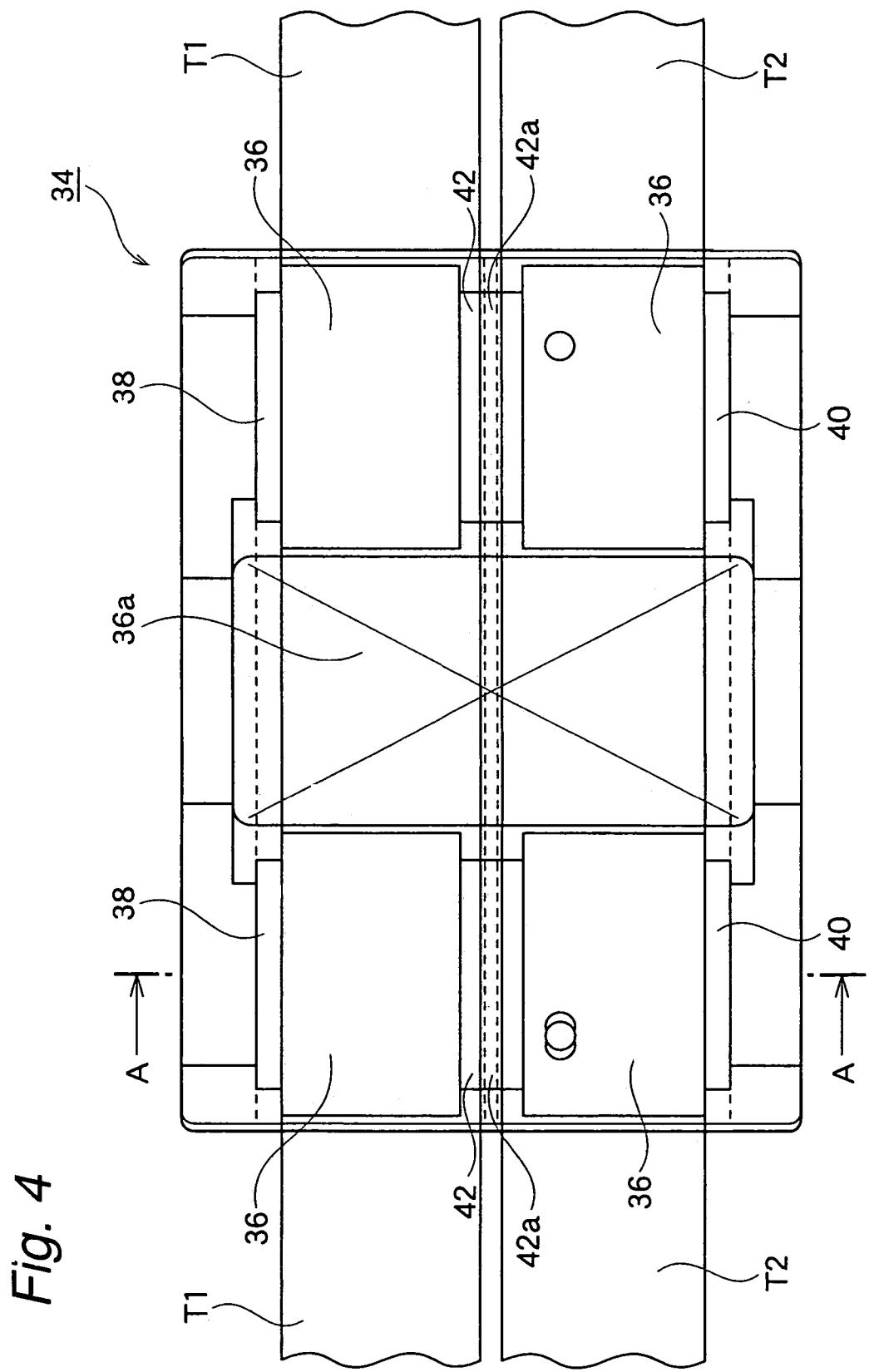
FIG. 4 is a perspective view showing a guide member in an inspecting section.
Figure 5:
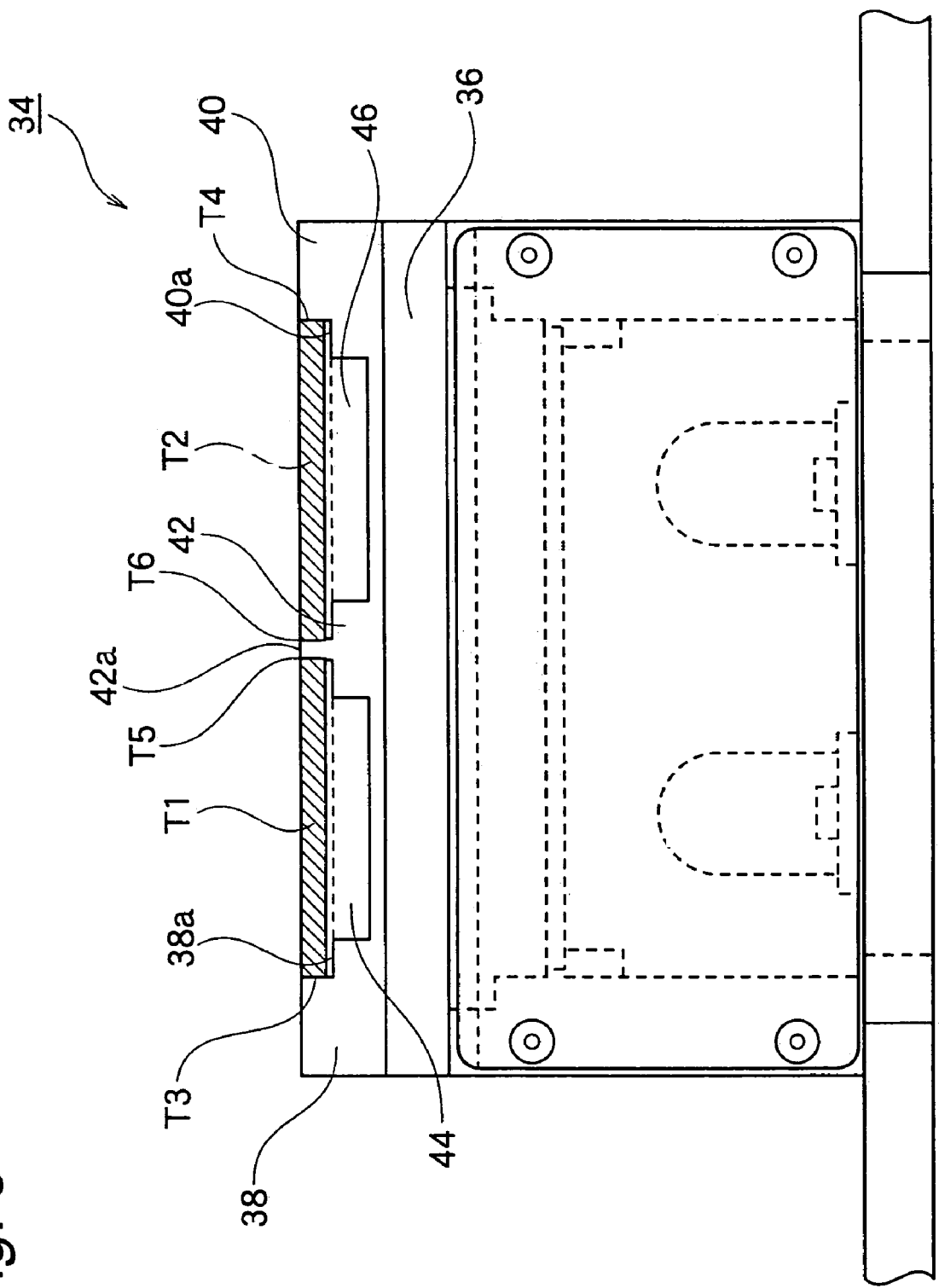
FIG. 5 is a sectional view taken along a line A-A in FIG. 4.
Figure 6:
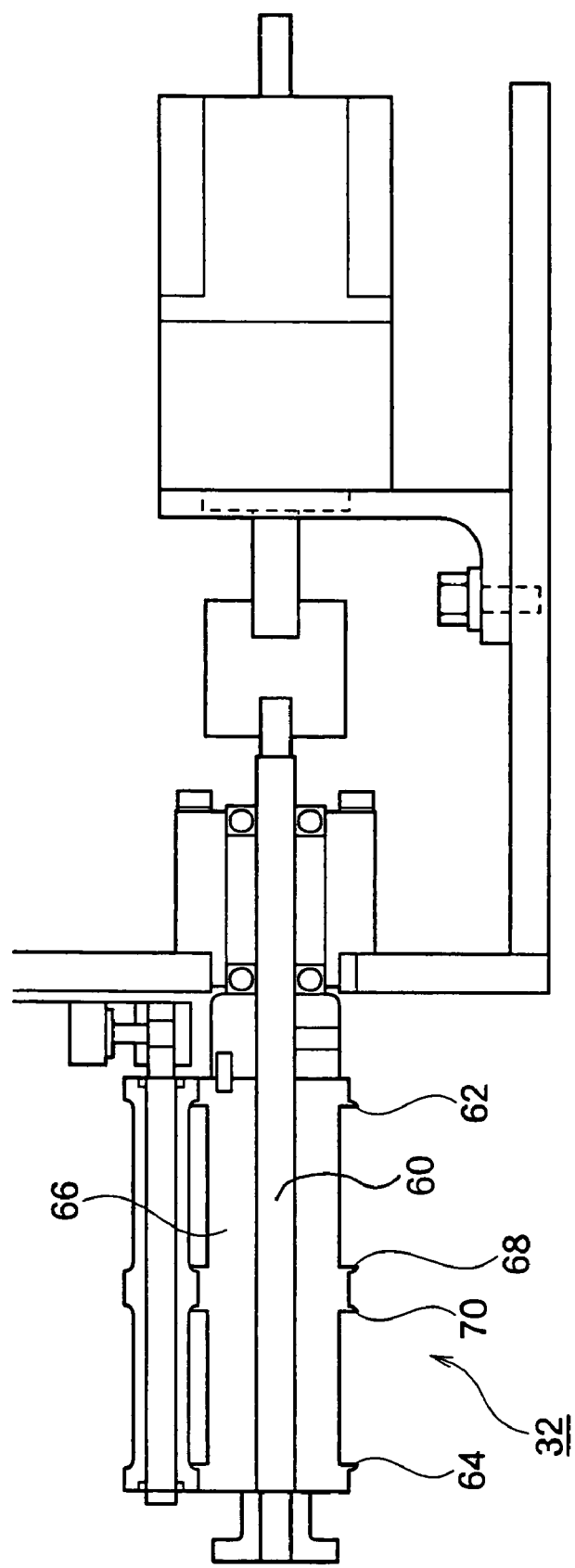
FIG. 6 is a sectional view showing a drive gear.
Figure 7:
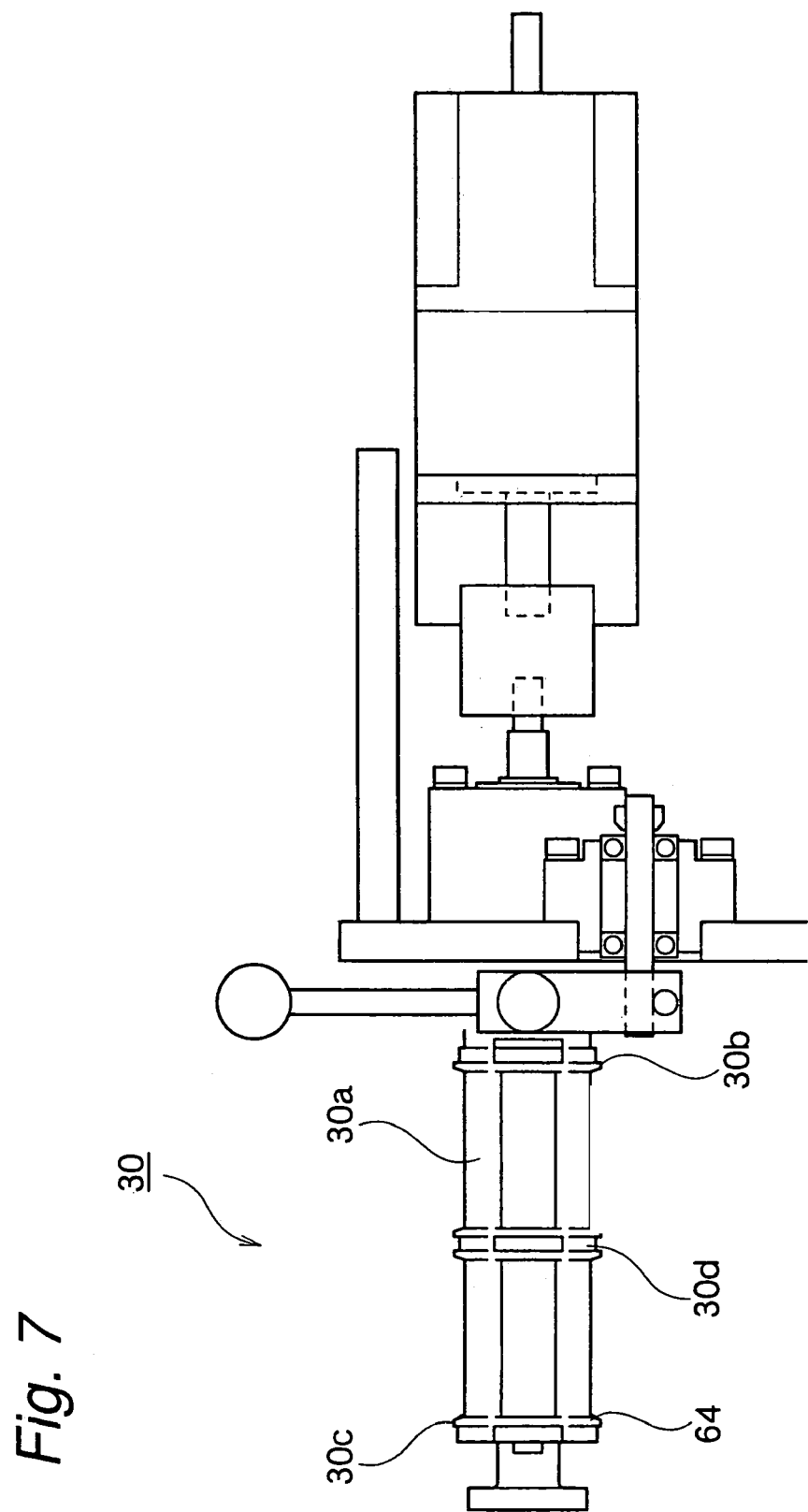
FIG. 7 is a sectional view showing a back tension roller.
Figure 8:
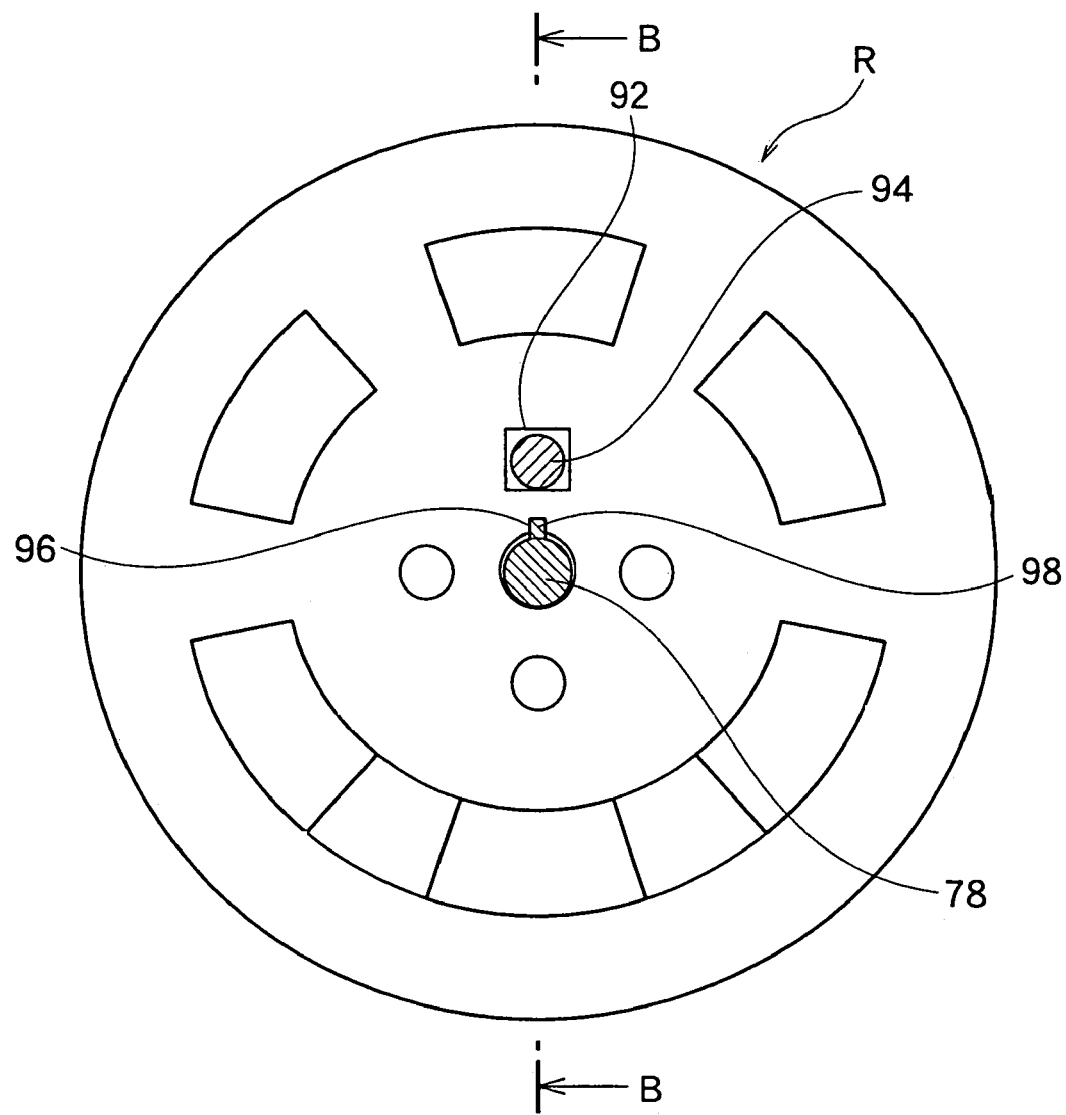
FIG. 8 is a front view showing the reel portion of a take-up device.
Figure 9:
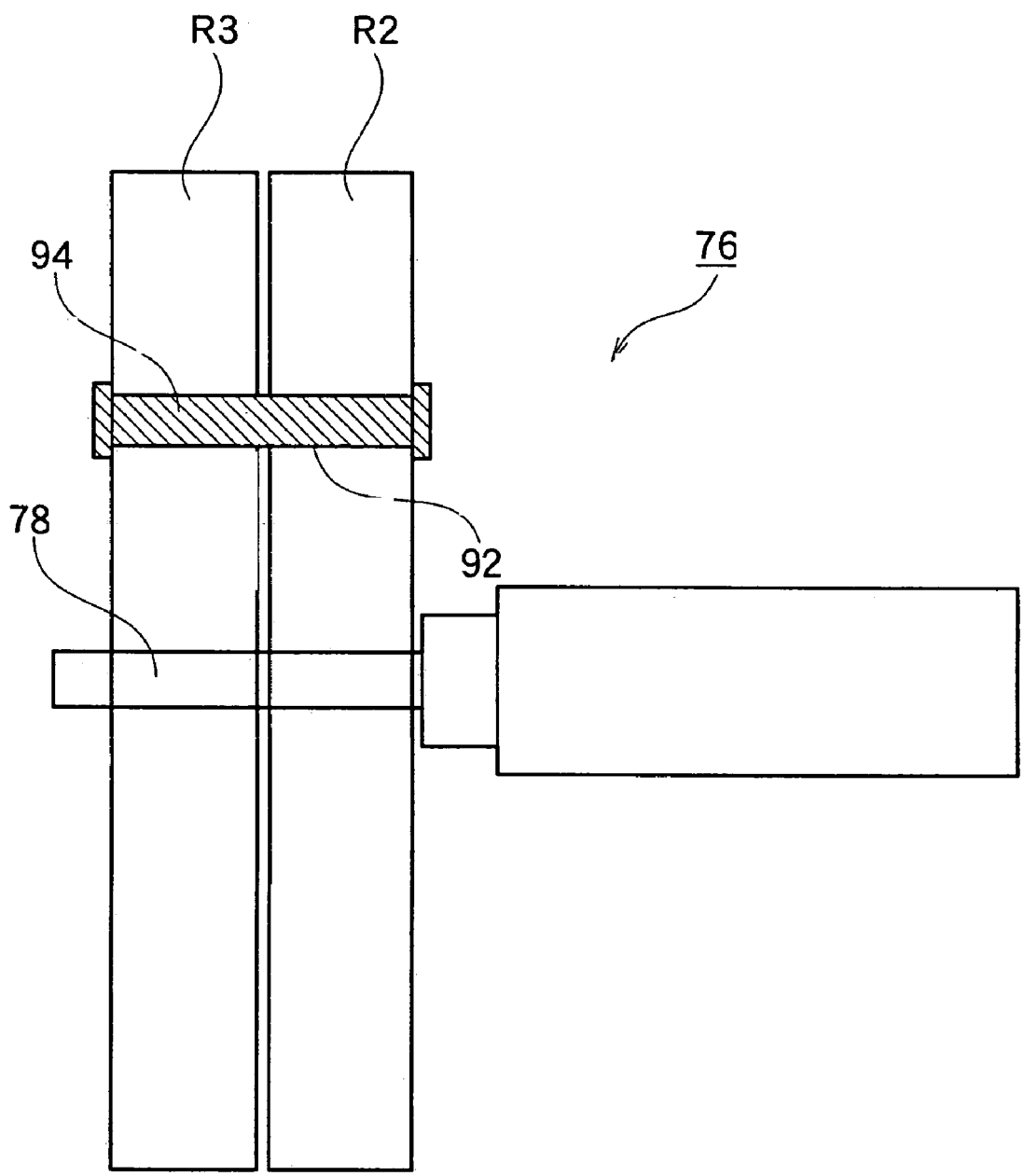
FIG. 9 is a sectional view taken along a line B-B in FIG. 8.
Figure 10:
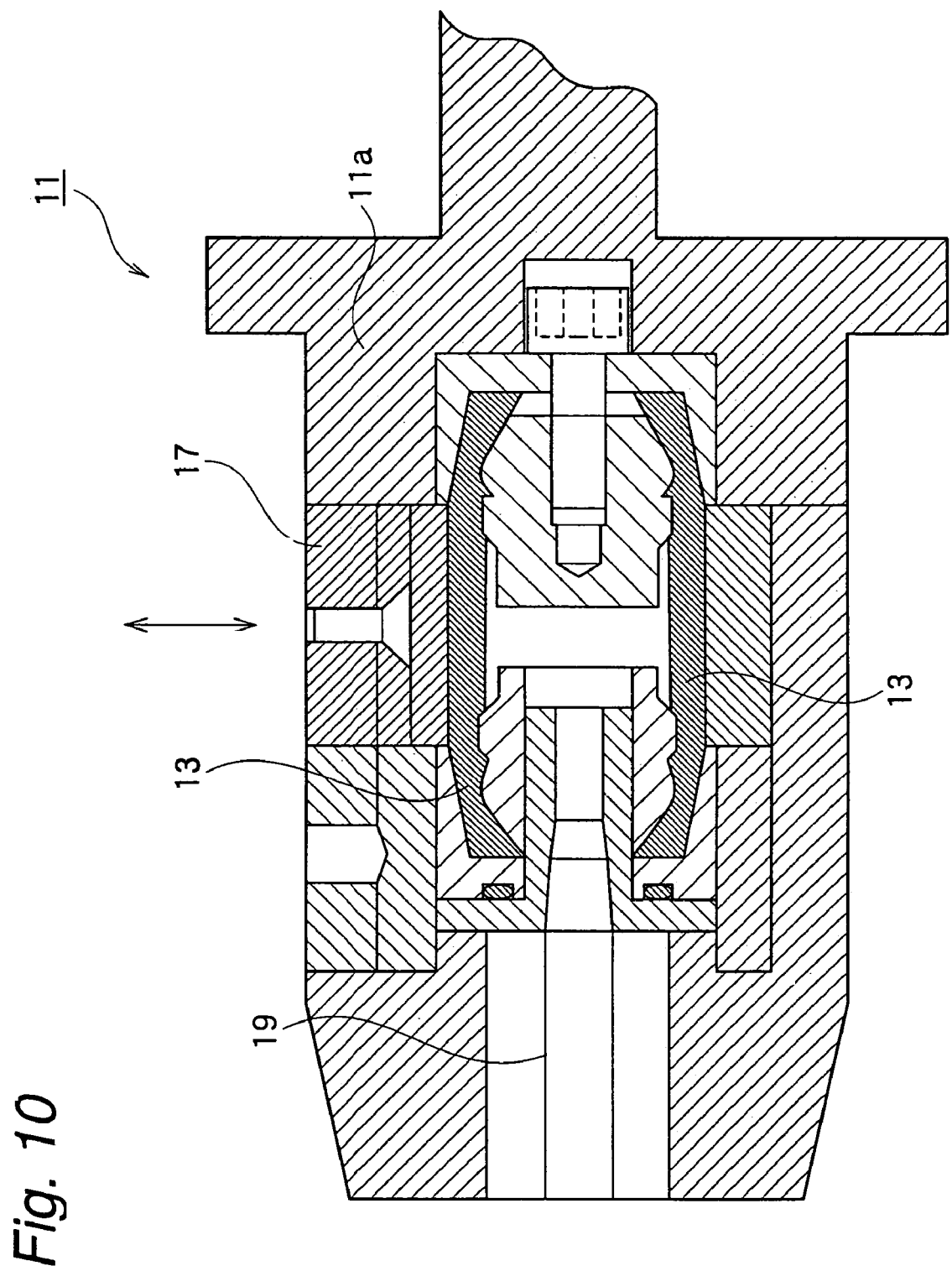
FIG. 10 is a sectional view showing an air shaft.

FIG. 1 is a front view showing an apparatus for inspecting a film carrier tape for mounting electronic component according to an embodiment of the present invention, FIG. 2 is a schematic view for explaining a method for inspecting a film carrier tape for mounting electronic component according to the present invention, FIG. 3 is a top view showing a film carrier tape for mounting electronic component which is used in the apparatus for inspecting a film carrier tape for mounting electronic component according to the present invention, FIG. 4 is a perspective view showing a guide member in an inspecting section, FIG. 5 is a sectional view taken along a line A-A in FIG. 4, FIG. 6 is a sectional view showing a drive gear, FIG. 7 is a sectional view showing a back tension roller, FIG. 8 is a front view showing the reel portion of a take-up device, FIG. 9 is a sectional view taken along a line B-B in FIG. 8, and FIG. 10 is a sectional view showing an air shaft.

As shown in FIG. 1, 10 wholly denotes an apparatus for inspecting a film carrier tape for mounting electronic component according to the present invention (which will be hereinafter referred to as an "inspecting apparatus").

As shown in FIG. 1, in the inspecting apparatus 10, a reel R1, upon which a film carrier tape for mounting electronic component such as TAB, CSP or BGA, that is, a film carrier tape T for mounting electronic component which has completely been subjected to a manufacturing process thereof (which will be hereinafter referred to as a "film carrier tape") is wound through a spacer S, is attached to an unwinding driving shaft 14 of an unwinding device 12.

By the driving operation of a driving motor, the unwinding driving shaft 14 is rotated so that the film carrier tape T is reeled out from the reel R1 together with the spacer S and is supplied to an inspecting section 20 through guide rollers 16 and 18.

The film carrier tape T is a film carrier tape for mounting electronic component, in which a plurality of electronic component mounting portions G (referred to as so-called "multiple take-up") is provided in multiple strips in a transverse direction as shown in FIG. 3.

In the present embodiment, for convenience of description, there is shown a film carrier tape for mounting electronic component in which two electronic component mounting portions G1 and G2 are provided in two strips in the transverse direction of the film carrier tape T. For example, it is possible to use a film carrier tape portion having a width of 48 mm in two strips(48 mm×2), a film carrier tape portion having a width of 35 mm in two strips (35 mm×2) and the like.

In order to inspect the portions of the film carrier tapes to be inspected, which are enlarged by a microscope 48 and a magnifying glass 50 in the inspecting section 20, within the same field of view, as will be described below, it is desirable that the sum of the widths of the film carrier tapes in a plurality of strips should be 160 mm or less, preferably 130 mm or less and more preferably 110 mm or less.

As shown in FIG. 1, the unwinding device 12 is provided with three position sensors 22 in a vertical direction. When a lower end T' of the loosened portion of the film carrier tape T (T1, T2), which is cut and separated into individual strips, is detected by the lower position sensor, the driving operation of the driving motor of the unwinding device 12 is stopped to prevent the film carrier tape for mounting electronic component from being excessively loosened to damage a floor in contact therewith.

When the lower end T' of the loosened portion of the film carrier tape T (T1, T2) is detected by the upper position sensor 22, moreover, the driving operation of the driving motor of the unwinding device 12 is started to maintain a constant looseness of the film carrier tape for mounting electronic component.

In FIG. 1, 24 denotes a dancer roller which serves to maintain the tension of the film carrier tape T (T1, T2) to be constant by a dead weight thereof.

Thus, the film carrier tape T, which is unwound out from the unwinding device 12 and conveyed, is cut into individual film carrier tapes in strips through a slit device 26 including a cutting blade, and is cut into strips and is separated into individual film carrier tapes T1 and T2 as shown in FIG. 2.

The film carrier tapes T1 and T2, which are thus obtained by cutting and separating the film carrier tape T into strips through the slit device 26, pass through the guide rollers 16 and 18, respectively.

The film carrier tapes T1 and T2 passing through the guide rollers 16 and 18 are supplied to the inspecting section 20.

The film carrier tape T supplied to the inspecting section 20 is conveyed by means of a back tension roller 30 and a drive gear 32.

When passing through a part between the back tension roller 30 and the drive gear 32, the driving operation of the drive gear 32 is stopped temporarily. As a result, the supply of the film carrier tape T is stopped and a portion to be inspected is stopped in a predetermined position of the inspecting section 20, that is, an inspecting position P.

In this case, the film carrier tape T (T1, T2) is accurately placed in a predetermined position by the reverse rotation of the back tension roller 30 to be engaged with the sprocket hole of the film carrier tape T (T1, T2), for example, and is positioned based on the sprocket hole of the film carrier tape T (T1, T2).

More specifically, the driving operation of the drive gear 32 is temporarily stopped through a control device 15 as shown in FIG. 1 so that the supply of the film carrier tape T (T1, T2) is stopped.

In this case, the rotation of the drive gear 32 is carried out by controlling an internal pulse obtained by the rotation of a pulse motor, which is to be a driving mechanism for driving the drive gear 32.

Instead of controlling the internal pulse obtained by the rotation of the pulse motor, which is to be the driving mechanism for driving the drive gear 32, to control the stoppage of the conveyance of the film carrier tape, the controlling of rotation of the drive gear 32 can also be carried out by detecting a position in a longitudinal direction of the film carrier tape T (T1, T2), by means of a light irradiating device for irradiating a light such as a laser beam and a photoreceiving sensor through the sprocket hole of the film carrier tape T (T1, T2).

The stop position is set in such a manner that an electronic component mounting portion G of the film carrier tape T (T1, T2) to be inspected is placed in the predetermined position of a guide member 34, which is provided in the inspecting section 20, that is, the inspecting position P.

As shown in FIGS. 4 and 5, the guide member 34 serves to cause the film carrier tapes T1 and T2 cut into strips to run in parallel with each other.

The guide member 34 comprises side guide portions 38 and 40 on both ends, which have almost U-shaped sections, which are protruded upward from both ends of a bottom plate portion 36, and which serve to guide both end side portions T3 and T4 of the film carrier tape T on an outermost side.

The side guide portions 38 and 40 are provided with step portions 38a and 40a respectively, and the both end side portions T3 and T4 of the film carrier tape T on the outermost side are guided along the step portions 38a and 40a.

Moreover, an adjacent part guide portion 42, which is protruded upward from the bottom plate portion 36 and having a flat upper surface, is provided between the side guide portions 38 and 40 on both ends, so that adjacent side portions T5 and T6 of the film carrier tape cut into strips can be guided.

Furthermore, a separating protruded portion 42a is provided in the upper part of the adjacent part guide portion 42, so that the adjacent side portions T5 and T6 of the film carrier tape is prevented from being worn away and damaged in contact with each other. The width of the separating protruded portion 42a is not particularly restricted but is suitably set to be approximately 3 mm in consideration of a separating effect.

Consequently, spaces 44 and 46 are formed between the side guide portions 38 and 40 and the adjacent part guide portion 42 in such a manner that the film carrier tape T (T1, T2) can be prevented from being damaged by a friction or the like in conveyance.

By such a structure, all the adjacent side portions T5 and T6 of the film carrier tapes T1 and T2 cut into strips and side portions on both ends are supported and guided by the side guide portions 38 and 40 and the adjacent part guide portion 42 in the guide member 34.

In the inspecting section 20, accordingly, the film carrier tapes T1 and T2 running in parallel are not curled in a transverse direction, that is, are not flexed respectively. Consequently, the inspecting position P, that is, the focal position of a magnifying lens or the like is maintained to be constant as will be described below. As a result, a quality inspection requiring very high precision in the pattern defects of the bend, flaw and the like of an inner lead can be carried out accurately with high precision without a shift of the focal point of a magnifying glass or the like.

In the present embodiment, since the film carrier tapes T1 and T2 in two strips are used, one middle adjacent part guide portion 42 is provided. It is preferable to properly regulate the number of the adjacent part guiding portions 42 and an interval therebetween depending on the number of strips of the film carrier tape T.

Moreover, it is desirable that the adjacent side portions T5 and T6 of the film carrier tapes T1 and T2 should be guided and conveyed by means of the guide member 34 with a slight gap so as not to be worn away and damaged in contact with each other.

As shown in FIG. 1, the inspecting section 20 is provided with a magnifying lens device for executing, by human eyes, a visual inspection for a disconnection, a short circuit, a dent (i.e. reducing portion of wiring lead width), a projection and a plating defect, a deformation of the shape of the tape, and a defect of solder resist or the like, for example, in the wiring portion of a film carrier tape having a wiring pattern pitch of 35 μm or more, preferably 40 μm or more by utilizing a reflected light or a transmitted light, for example.

It is desirable that the magnifying lens device should be constituted by a microscope 48 having a plurality of lenses combined, and a magnifying glass 50 having one lens.

In this case, it is preferable that the inspecting section 20 should be provided with the magnifying glass 50 for carrying out the visual inspection on this side of the microscope 48.

In this case, it is desirable that the magnifying lens device should have a power of 1.4 or more, a power of 1.4 to 6.0, preferably a power of 1.5 to 3.5 and further preferably a power of 1.8 to 3.0 for a magnification at an enlargement ratio of a length.

More specifically, a defective product cannot be sufficiently detected when the magnification of the magnifying lens device is a power of less than 1.4, and a pattern goes beyond a field of view if the magnification is a power of more than 6.

In case of a magnifying glass having one lens, specifically, it is suitable that the magnification should be a power of 1.5 to 2.5. In case of a stereoscopic microscope having a plurality of lenses, moreover, it is suitable that the magnification should be a power of 2 to 6. As will be described below, in some cases in which a pattern seeming to be a defective product is inspected in detail, the magnification is raised to be a power of approximately 20, thereby carrying out the inspection.

More specifically, in a method for inspecting a film carrier tape by using the magnifying lens device, ① A magnification is set to be a power of 2 to 6, for example, in such a manner that a plurality of patterns comes in sight at the same time, ② In principle, the inspection is carried out without a change in the magnification. When a pattern which seems to be defective is found and is to be inspected in detail, ③ In the case in which the magnifying glass 50 is used, a position thereof is shifted to carry out the inspection with a magnification of a power of approximately 20, for example, by using a stereoscopic microscope 48 having a high magnification, and ④ In the case in which the stereoscopic microscope 48 is used at a low magnification of a power of 2 to 6, for example, the magnification is changed to be high and the inspection is carried out at a magnification of a power of approximately 20, for example.

With respect to the film carrier tapes T1 and T2 cut into strips and running in parallel with each other which are guided by the guide member 34, moreover, the magnifying lens device serves to execute the inspection for two lines at the same time in the total width directions of the film carrier tapes T1 and T2.

Furthermore, the magnifying glass 50 is constituted by a magnifying lens for magnifying the film carrier tape. Although such a lens is not particularly restricted, a glass lens or a Fresnel lens having a magnification of a power of approximately 1.5 to 2.5 can be used, for example.

In the inspecting section 20, it is sufficient that a plurality of patterns comes in sight when the inspection is to be carried out by the magnifying lens device. If the relative positions of the film carrier tapes in plural strips come in the same sight, they do not need to be accurately coincident with each other but may be shifted from each other.

As shown in FIG. 2, furthermore, the inspecting section 20 comprises an illuminating device 52 for irradiating a light on the film carrier tape to be inspected. As shown in FIG. 2, the illuminating device 52 includes illuminating lamps 54 and 54, which are provided apart from each other at a constant interval in an upper part behind the inspecting section 20.

The illuminating lamps 54 and 54 have such a structure that a light is simultaneously focused on the inspecting position P from rearward and above for the film carrier tape T (T1, T2).

Consequently, the whole widths of the film carrier tapes for mounting electronic component which run in parallel are illuminated greatly. Therefore, an accurate quality inspection with high precision can be simultaneously carried out over a plurality of film carrier tapes for mounting electronic component.

The periphery of field of view is dark around the lens when the film carrier tape is inspected through the microscope. In order to compensate for the darkness, a light may be irradiated from the side surfaces of the film carrier tape T (T1, T2) altogether or singly.

In addition, the illuminating device 52 gives a bright illumination. Consequently, a light which is irradiated from the ceiling of the inspection room and reflected by the film carrier tape T is relieved. Therefore, it is possible to carry out an accurate quality inspection with high precision without hindering the inspection of the film carrier tape through the reflected light.

In FIG. 1, 56 denotes a transmitted light irradiating device which is used for carrying out a visual inspection through a transmitted light. In order to provide for the case in which the transmitted light irradiating device 56 is used, an opening portion 36a for the transmission of the transmitted light is preformed on the bottom plate portion 36 of the guide member 34 in the inspecting position P.

There is additionally provided an input switch for deciding an excellent product or a defective product through an inspection carried out by the microscope 48 and the magnifying glass 50 and for inputting a position thereof in the inspection executed in the inspecting section 20, which is not shown. Consequently, a position in a predetermined order of the electronic component mounting portion G, a position in a longitudinal direction of the tape in a defective part, and a position in a transverse direction are input to the control device 15.

Referring to the switch, for example, a left hand side switch serves as an ON/OFF switch of a driving motor, which is not shown. With respect to a right hand side switch, moreover, two switches are provided on the near side and on the back side. The respective switches are pressed corresponding to the film carrier tapes T1 and T2. A defect mark is put on a product on the inner side when the switch on the inner side is pressed. A defect mark is put on a product on this side when the switch on this side is pressed. Thus, a mark for a defective product can be put.

Based on the result of the input of the control device 15, a defect display is given to a predetermined position by means of a defect display device 58 provided on the downstream side of the inspecting section 20. The defect display device 58 is not particularly restricted but it is possible to use any device capable of carrying out the defect display through punching, inking, dry ink (marker) or the like for a defective product.

As shown in FIG. 6, the drive gear 32 includes a shaft portion 60, both end gears 62 and 64 provided on both ends of the shaft portion 60, a roller body 66 formed of a synthetic resin such as PTFE (polytetrafluoroethylene) (MC nylon) or fluororesin which is provided around the shaft portion 60 between the both end gears 62 and 64, and intermediate gears 68 and 70.

In this case, the both end gears 62 and 64 are constituted to be mated with sprocket holes H3 and H4 on the side portions T3 and T4 on both ends of the film carrier tape T on the outermost side, respectively.

Moreover, the intermediate gears 68 and 70 are constituted to be mated with sprocket holes H5 and H6, which are provided on the adjacent side portions T5 and T6 of the film carrier tapes cut into strips.

By such a structure, all of the sprocket holes H3 to H6, which are provided on the side portions T3 and T4 on both ends and the adjacent side portions T5 and T6 in the film carrier tapes T1 and T2 cut into strips, are mated with the both end gears 62 and 64 and the intermediate gears 68 and 70 in the drive gear 32 and are simultaneously conveyed at equal speeds to each other.

In the inspecting section 20, accordingly, the positions of the film carrier tapes T1 and T2 running in parallel with each other are not shifted from each other. Consequently, it is possible to simultaneously carry out an accurate quality inspection with high precision over a plurality of film carrier tapes.

Moreover, the whole film carrier tape T (T1, T2) is supported by the roller body 66. In the driving operation, therefore, a driving force is not centralized on the gear so that the sprocket holes can be prevented from being damaged.

In the present embodiment, the film carrier tapes T1 and T2 in two strips are used. For this reason, two intermediate gears 68 and 70 are provided and the number and interval of the intermediate gears 68 and 70 are preferably regulated properly depending on the number of multiple strips of the film carrier tape T.

Furthermore, the back tension roller 30 shown in FIG. 7 includes a roller body 30a, side guide protruded portions 30b and 30c on both ends which are protruded from both ends of the roller body 30a, and an adjacent part guide protruded portion 30d which is protruded from the middle part of the side guide protruded portions 30b and 30c on both ends.

The both end side portions T3 and T4 of the film carrier tape T on the outermost side are guided by the side guide protruded portions 30b and 30c on both ends. Moreover, the adjacent side portions T5 and T6 of the film carrier tapes T1 and T2 which are cut into strips are separated and guided between the side guide protruded portions 30b and 30c on both ends by the adjacent part guide protruded portion 30d.

By such a structure, the adjacent side portions T5 and T6 of the film carrier tapes T1 and T2 can be prevented from being worn away and damaged in contact with each other in conveyance. Consequently, quality can be enhanced, and furthermore, a winding shift or the like can be prevented from being caused in take-up.

While the guide rollers 16, 18, 72, 74, 82 and 84 are ordinary rollers, they may have the same structures as the structure of the back tension roller 30.

Thus, the film carrier tapes T1 and T2, which are subjected to the predetermined quality inspection in the inspecting section 20, and on which a defect display is given to predetermined positions by the defect display device 58, pass through the guide rollers 72 and 74 and are taken up by a take-up device 76.

More specifically, the film carrier tapes T1 and T2 are constituted to be simultaneously taken up over a plurality of take-up reels R2 and R3 which are attached in parallel to the identical take-up driving shaft 78 of the take-up device 76. In this case, the film carried tapes T1 and T2 are taken up at equal speeds respectively by the rotation of the take-up driving shaft 78 through the driving operation of a driving motor which is not shown.

In this case, as shown in FIG. 1, spacers S1 and S2, which are reeled by the reel R1 of the unwinding device 12 and cut and separated in two strips by a slit device 80 in the same manner as in the film carrier tapes T1 and T2, are supplied to reels R2 and R3 through guide rollers 82 and 84.

In this case, the film carrier tapes T1, T2 are respectively wound around the reels R2, R3 together with the each spacers S1, S2. As a result, the film carrier tapes T1, T2 are respectively sandwiched by the each spacers S1, S2. Consequently, ink can be prevented from sticking to other portions due to the contact of the film carrier tapes and the film carrier tapes can be protected against damage.

While the spacer S is cut into two strips by the slit device 80 in the present embodiment, it may be separately taken up and used again without a slit carried out by the slit device 80. In this case, the spacers S1 and S2, which have already been cut to have predetermined dimensions, may be reeled from two other spacer unwinding reels R5 and R6 which are not shown. In addition, the film carrier tapes T1, T2 are respectively wound around the reels R2, R3 together with the each spacers S1, S2. As a result, the film carrier tapes T1, T2 are respectively sandwiched by the each spacers S1, S2.

The take-up device 76 is provided with three position sensors 88 in a vertical direction in the same manner as the unwinding device 12 as shown in FIG. 1. When a lower end T' of the loosened portion of the film carrier tape T (T1, T2) is detected by the lower position sensor, the driving motor of the take-up device 76 is driven to prevent the film carrier tape T (T1, T2) from being excessively loosened to damage a floor in contact therewith.

When the lower end T' of the loosened portion of the film carrier tape T (T1, T2) is detected by the upper position sensor 88, moreover, the driving operation of the driving motor of the take-up device 76 is stopped to maintain a constant looseness of the film carrier tape T.

The position sensors 88 are provided corresponding to the number of the film carrier tapes T1 and T2, respectively.

In FIG. 1, 90 denotes a dancer roller which serves to maintain the tension of the film carrier tape T (T1, T2) to be constant by a dead weight thereof.

For example, in case of a thin and light film carrier tape such as COF, it is preferable that the dancer rollers 24 and 90 should be used as in the present embodiment. In case of a thick film carrier tape having a great dead weight such as a general TAB tape, the dancer rollers 24 and 90 do not need to be used.

In the take-up device 76, furthermore, a removable engaging bar member 94 is inserted and fixed into a through hole 92 provided in the vicinity of the center of the reel, so that take-up reels R2 and R3, which are attached to the identical take-up driving shaft 78 of the take-up device 76 in parallel, are fixed to each other as shown in FIGS. 8 and 9.

In FIGS. 8 and 9, 96 denotes a key groove provided on the reel and 98 denotes a key provided on the take-up driving shaft 78 to be engaged with the key groove 96. By their engagement, the rotation of the take-up driving shaft 78 is transmitted to the reel.

In this case, the engaging bar member 94 is preferably removable, and a structure thereof is not particularly restricted but a well-known structure such as a bolt-nut type or a clamper type can be employed.

By such a structure, the take-up reels R2 and R3 are not shifted from each other during take-up. Consequently, the take-up can be carried out in the same take-up method at an equal speed. Therefore, it is possible to simultaneously obtain a film carrier tape in the same winding way without generating a winding shift.

In addition, where the reels R2 and R3 are attached to the separate driving shafts, if the center thereof is coincide, the detachable engaging bar member 94 can be inserted in to the through holes 92 as mentioned above.

Moreover, the take-up driving shaft 78 itself may be constituted by an air shaft capable of expanding to increase a diameter thereof by the supply of air.

FIG. 10 is a sectional view showing such an air shaft.

An air shaft 11 comprises a barrel-shaped balloon member 13 provided in an air shaft body 11a and a plurality of chuck members 17 is provided on the outer periphery of the balloon member 13. They are provided apart from each other at a constant angle and can be protruded freely.

The air is fed from an air source (not shown) through an air pipe line 19 into the balloon member 13 so that the chuck member 17 frequently appears as shown in an arrow of FIG. 10 so that a diameter can be increased freely.

By such a structure, the take-up reels are not shifted from each other during the take-up. Consequently, the take-up can be carried out in the same take-up method at an equal speed. Therefore, it is possible to simultaneously obtain the film carrier tapes for mounting electronic component in the same winding way without generating a winding shift.

In addition, in this case, it is possible to control the attachment, removal and fixation of the take-up reel, and a fixing force and a winding unevenness by regulating the supply and release of the air and an air pressure. Consequently, a very excellent convenience can be obtained and a complicated work is not required.

In the case in which the air shaft is used, when it is detected by the position sensor 88 that the degrees of looseness of the film carrier tapes T1 and T2 are different from each other, it is desirable that the air supply of the air shaft can be automatically released and the fixation of the reels R2 and R3 can be released to regulate the winding unevenness by the control of the control device 15.

In the dancer roller 24 of the unwinding device 12, the unwinding speeds of the film carrier tapes T (T1, T2) cut into strips are slightly different from each other. In the identical dancer roller 24, thus, the amounts of looseness of the film carrier tapes T (T1, T2) cut into strips are different from each other. Consequently, the identical dancer roller 24 is inclined.

When the dancer roller 24 is thus inclined, the amount of the looseness cannot be controlled smoothly and the film carrier tapes T (T1, T2) come in contact with each other and are thereby worn away and damaged.

For this reason, as shown in FIG. 1, it is desirable that a guide member 21 and a guide roller 23 comprising rollers or the like, which serve to separately change a guide path respectively, should be provided together with a horizontal sensor (not shown) for the film carrier tapes in strips which are to be guided by the identical dancer roller 24.

More specifically, as shown in FIG. 1, when the film carrier tape in each strip to be guided by the dancer roller 24 is loosened as in a position shown in a solid position, the guide member 21 is moved horizontally in a direction of an arrow as shown in a dotted line. As a result, the film carrier tape T (T1, T2) and the identical dancer roller 24 can be guided by the guide roller 23 and can be moved to a position shown in a dotted line, thereby eliminating the looseness. Namely, the identical dancer-roller 24 can be disposed in a horizontal position. To the contrary, when the looseness is eliminated, it is preferable that the guide member 21 should be moved from the position shown in the dotted line to the position shown in the solid line.

When the identical dancer roller 24 is inclined, the amount of the looseness cannot be controlled smoothly and the film carrier tapes for mounting electronic component come in contact with each other and are worn away and damaged. However, by causing the guide member 21 to separately change the guide path for each strip, in this invention, it is possible to set the amount of the looseness to be equal. Thus, such a situation can be prevented effectively.

With respect to the dancer roller 90 of the take-up device 76, similarly, a guide member 71 and a guide roller 73 are provided in the same manner as shown in FIG. 1. Consequently, guide paths for respective strips are separately changed by the guide member 71 so that the amount of the looseness can be set to be equal. Thus, it is desirable to effectively prevent such a situation that the amount of the looseness cannot be controlled smoothly and the film carrier tapes for mounting electronic component come in contact with each other and are worn away and damaged.

Figure 11:
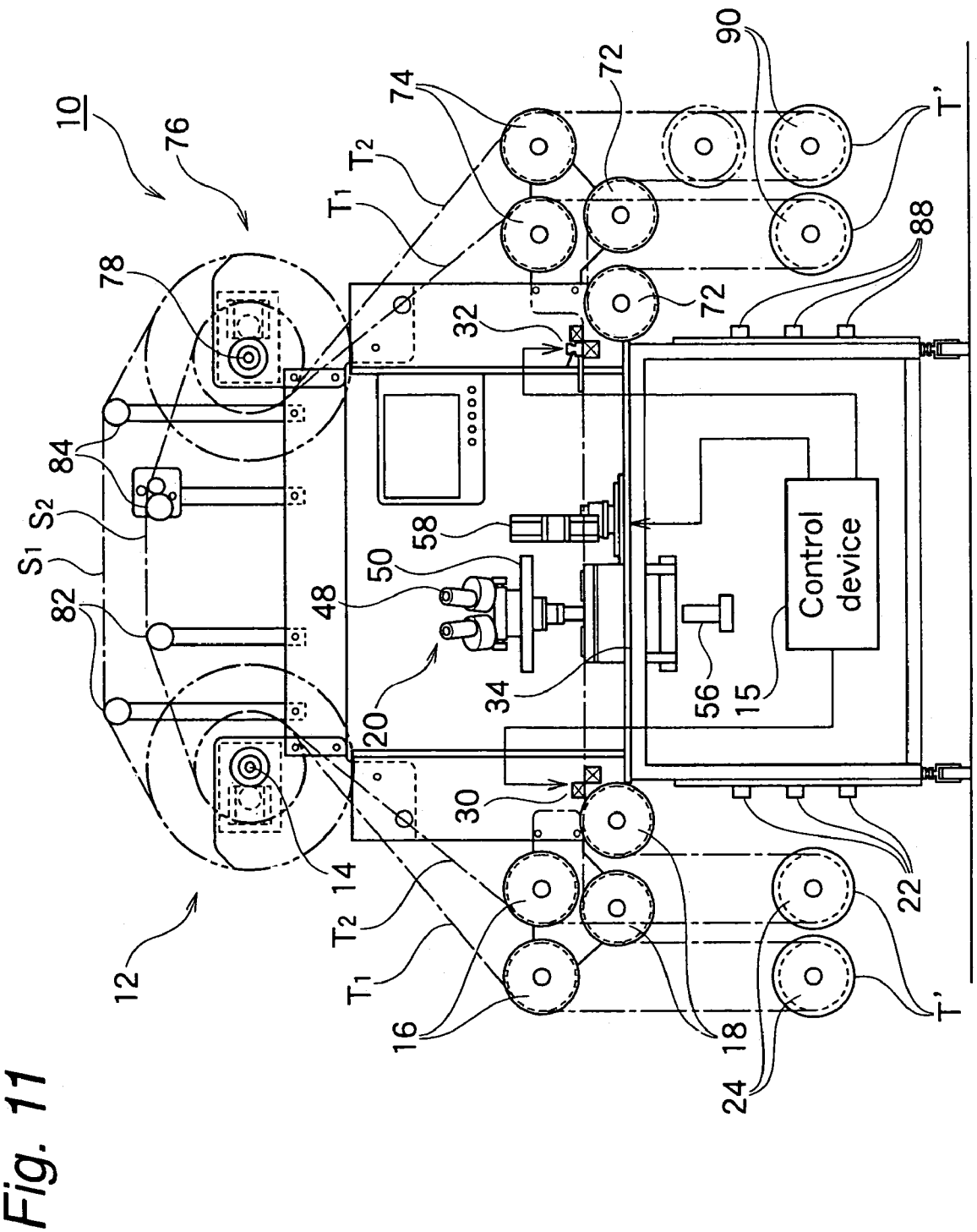
FIG. 11 is a front view showing an apparatus for inspecting a film carrier tape for mounting electronic component according to another embodiment of the present invention in the same manner as in the embodiment of FIG. 1.
Figure 12:
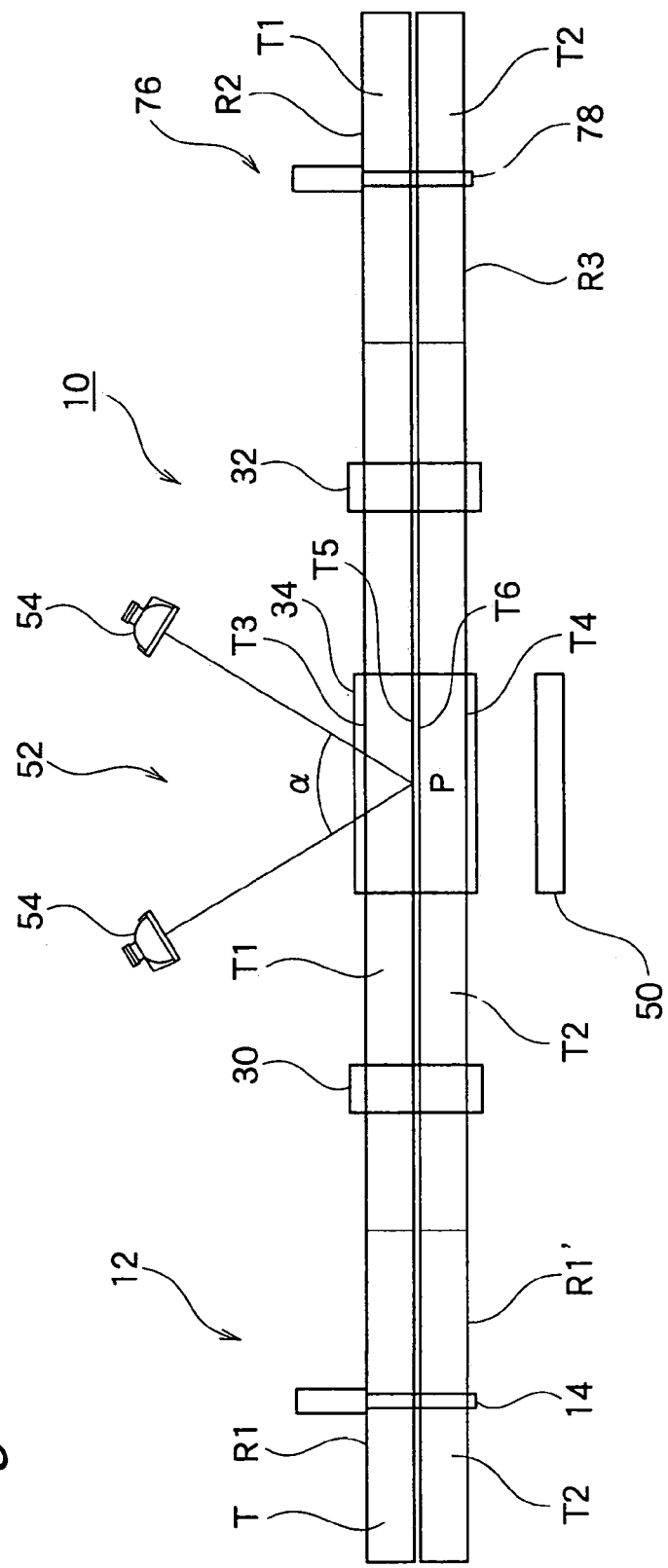
FIG. 12 is a schematic view for explaining a method for inspecting a film carrier tape for mounting electronic component according to the present invention in the same manner as in FIG. 2.
Figure 13:
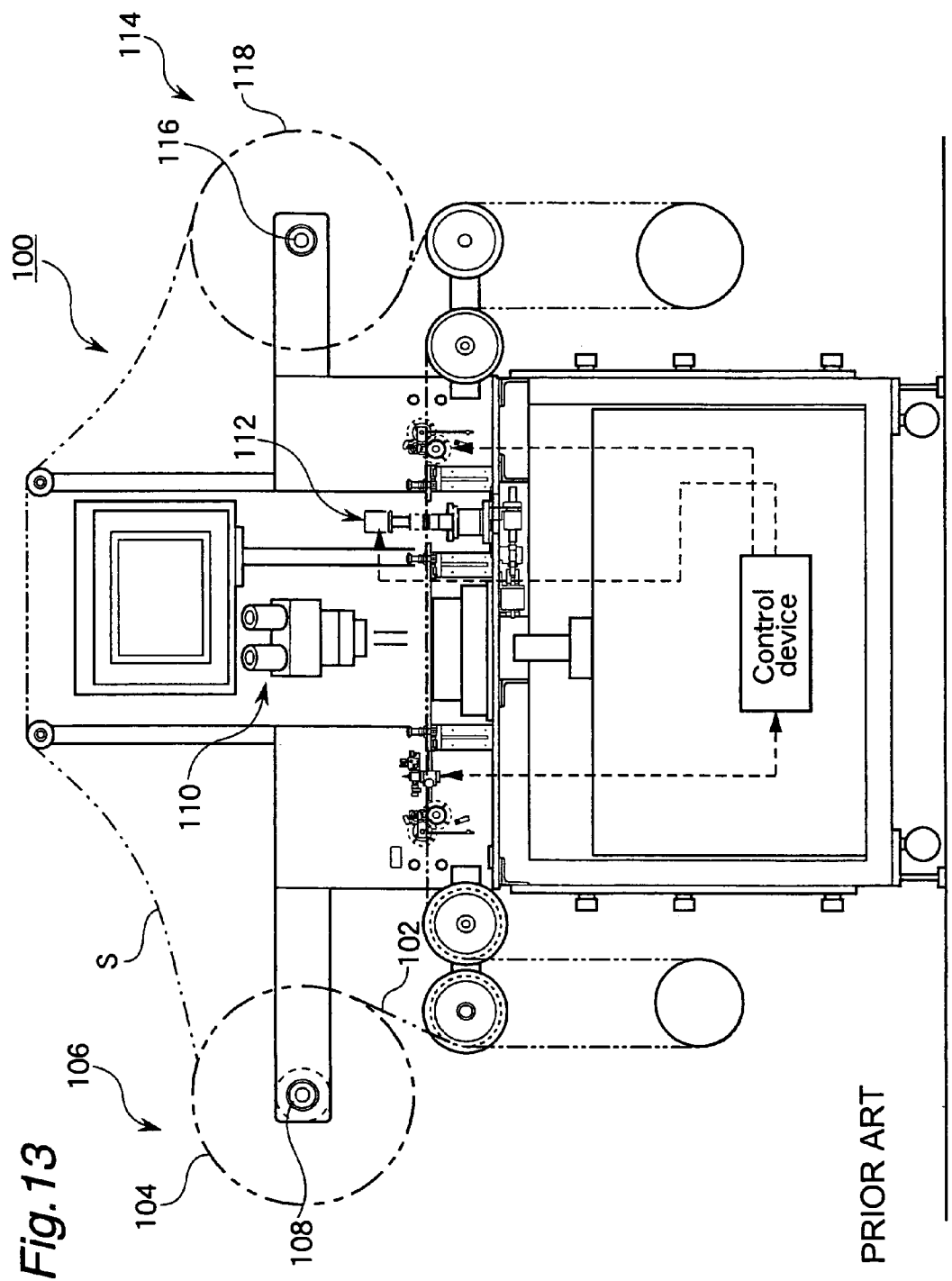
FIG. 13 is a front view showing an apparatus for inspecting a film carrier tape for mounting electronic component according to the conventional art.

FIG. 11 is a front view showing an apparatus for inspecting a film carrier tape for mounting electronic component according to another embodiment of the present invention in the same manner as in the embodiment of FIG. 1, and FIG. 12 is a schematic view for explaining a method for inspecting a film carrier tape for mounting electronic component according to the present invention in the same manner as in FIG. 2.

In the present embodiment, basically, the same structure as that of the film carrier tape inspecting apparatus 10 according to the embodiment shown in FIG. 1 is employed. Therefore, the same components have the same reference numerals and detailed description thereof will be omitted.

In a film carrier tape inspecting apparatus 10 according to the present embodiment, film carrier tapes T1 and T2, which are previously cut into individual film carrier tapes T1 and T2 in strips, are separately wound upon unwinding reels R1 and R1' of an unwinding device 12, respectively.

Correspondingly, spacers S1 and S2 cut previously are used for spacers.

In the present embodiment, accordingly, the slit devices 26 and 80 are not provided. In the present embodiment, moreover, each of guide rollers 16, 18, 72 and 74 is provided in two sets in order to separately guide the film carrier tapes T1 and T2.

Even if the film carrier tapes for mounting electronic component which are previously cut into the individual film carrier tapes for mounting electronic component in strips, are used, thus, the same functions and effects as those of the embodiment shown in FIG. 1 can be obtained.

In the film carrier tape inspecting apparatus according to the present embodiment, it is desirable that an engaging bar member 94 and an air shaft 11 should be used in the unwinding reels R1 and R1' of the unwinding device 12 to obtain the same unwinding rate at an equal unwinding speed, and to prevent the position of an electronic component mounting portion from being shifted in an inspecting section 20 and to hinder a winding unevenness and a shift from being generated in take-up.

Furthermore, in this specification the term "in parallel" means "back and forth, side to side, up and down, or at an angle".

While the preferred embodiments of the present invention have been described above, the present invention is not restricted thereto. Although a human visual inspection is executed in the inspecting section 20 according to the embodiments, for example, it is also possible to automatically carry out a quality inspection by image recognition through a CCD camera or the like, for example. Thus, various changes can be made without departing from the scope of the present invention.

Furthermore, in this specification the term "in parallel" means "back and forth, side to side, up and down, or at an angle".

Furthermore, the apparatus and the method for inspecting a film carrier tape of this invention are also applicable to appearance inspection of the film carrier tape on which electronic components are mounted.

According to the present invention, the individual film carrier tapes for mounting electronic component, which are previously cut into strips, are reeled out of the unwinding reel of the unwinding device, and run in parallel with each other and pass through the inspecting section in the cutting state without mutually causing a positional shift.

According to the present invention, moreover, the film carrier tapes for mounting electronic component, which are provided with a plurality of electronic component mounting portions in multiple strips in the transverse direction, are exactly used and unwound out from the unwinding device, and are exactly cut into individual film carrier tapes for mounting electronic component in multiple strips by means of the slit device.

The individual film carrier tapes for mounting electronic component in strips thus cut run in parallel with each other and pass through the inspecting section without mutually causing a positional shift.

Accordingly, the film carrier tapes for mounting electronic component in plural strips running in parallel can be subjected to a visual inspection to be an visual inspection (a transmitted light inspection and a reflected light inspection) simultaneously and accurately in the inspecting section. As a result of various quality inspections for a disconnection, a short circuit, a flaw, a projection and the like, a defect display can be carried out over a defective product through punching, inking, dry ink or the like.

Therefore, the film carrier tapes for mounting electronic component, which are provided with a plurality of electronic component mounting portions in multiple strips in the transverse direction, can be exactly used and inspected at a time. Thus, an inspection efficiency and inspection precision can be enhanced very greatly.

In addition, it is possible to mutually separate the individual film carrier tapes for mounting electronic component in strips without mutually causing a positional shift and to take up the same tapes upon the individual reels without a winding shift after the inspection.

More specifically, according to the present invention, an inspection processing can be carried out continuously and accurately in large quantities, a processing efficiency can be enhanced very greatly, and furthermore, the processing can be carried out by one operator so that a cost can be reduced.

According to the present invention, furthermore, all the adjacent side portions and the side portions on the both ends of the film carrier tapes for mounting electronic component which are cut into strips are supported and guided by the side guide portion and the adjacent part guide portion in the guide member.

In the inspecting section, accordingly, the film carrier tapes for mounting electronic component, which are caused to run in parallel, are not curled in the transverse direction, that is, are not flexed respectively. Consequently, inspecting positions are constant. As a result, it is possible to carry out an accurate quality inspection with high precision without shifting the focal point of a magnifying glass or the like in a requirement for very high precision for an inner lead bend, a flaw and the like.

According to the present invention, moreover, all of the sprocket holes, which are provided in the adjacent side portions and the side portions on the both ends of the film carrier tapes for mounting electronic component, which are cut into strips, are mated with the both end gears and the intermediate gear in the drive gear, and they are simultaneously delivered at an equal speed.

In the inspecting section, accordingly, the positions of the film carrier tapes for mounting electronic component, which are caused to run in parallel, are not shifted from each other. Therefore, it is possible to simultaneously carry out an accurate quality inspection with high precision for a plurality of film carrier tapes for mounting electronic component.

According to the present invention, furthermore, the adjacent side portions of the film carrier tapes for mounting electronic component, which are cut into strips, are guided in a mutual separating state by the adjacent part guide protruded portion in the guide roller.

In the conveyance, therefore, the adjacent side portions of the film carrier tapes for mounting electronic component can be prevented from coming in contact with each other and being worn away and damaged. Consequently, quality can be enhanced and a winding shift or the like can be prevented from being caused in the take-up.

According to the present invention, moreover, the take-up reels, which are attached to the identical take-up shaft of the take-up device in parallel with each other, are fixed to each other by means of the engaging bar member which are inserted in the through holes provided in the vicinity of the centers of the reels.

Accordingly, the take-up reels are not shifted from each other in the take-up, and the take-up is carried out at an equal speed in the same take-up way. Consequently, it is possible to simultaneously obtain a film carrier tape for mounting electronic component in the same winding form without generating a winding shift.

According to the present invention, furthermore, the air is supplied to the air shaft constituting the take-up shaft. Consequently, the shaft is expanded and increased in a diameter so that a plurality of take-up reels, which are attached to the identical take-up shaft of the take-up device in parallel with each other, are fixed to each other.

Accordingly, the take-up reels are not shifted from each other in the take-up, and the take-up is carried out at an equal speed in the same take-up way. Consequently, it is possible to simultaneously obtain a film carrier tape for mounting electronic component in the same winding form without generating a winding shift.

In addition, in this case, it is possible to control the attachment, removal and fixation of the take-up reel, a fixing force and a winding unevenness by regulating the supply and release of air and an air pressure. Consequently a very great convenience can be obtained and a complicated work is not required.

According to the present invention, furthermore, the film carrier tape for mounting electronic component in the total width direction can be enlarged through the magnifying lens device. Consequently, it is possible to simultaneously carry out an accurate quality inspection with high precision for a plurality of film carrier tapes for mounting electronic component.

According to the present invention, moreover, when the film carrier tapes for mounting electronic component which are cut into strips are unwound and taken up by means of the identical dancer roller, for example, they are unwound for the strips and the dancer roller is inclined due to a slight difference in a take-up speed. Therefore, the amount of the looseness cannot be controlled smoothly so that the film carrier tapes for mounting electronic component come in contact with each other and are thus worn away and damaged. However in this invention, by separately changing the guide path for each strip by means of the guide member, the amount of the looseness can be set to be equal. Therefore, such a situation can be prevented effectively. Thus, the present invention is so excellent as to produce various functions and effects.

What is claimed is:

1. An apparatus for inspecting a film carrier tape for mounting electronic component in which a plurality of electronic component mounting portions is provided in multiple strips in a transverse direction, comprising:
   an unwinding device for unwinding the film carrier tape for mounting electronic component in the multiple strips in which the individual film carrier tapes for mounting electronic component previously cut and separated into the individual strips are wound upon an unwinding reel, respectively;
   a back tension roller;
   an inspecting section for simultaneously inspecting the film carrier tapes for mounting electronic component, which are cut into strips, while causing them to run in parallel with each other;
   a drive gear;
   a take-up device for simultaneously taking up the film carrier tapes for mounting electronic component cut into strips, which are inspected in the inspecting section upon a plurality of take-up reels attached to an identical take-up shaft in parallel, respectively; and
   wherein the apparatus further comprises a guide member located at the inspection section for causing the cut strips of film carrier tapes to run in parallel with each other, the guide member comprising:
   a side guide portion formed on opposed transverse ends of the guide member to guide opposed outermost sides of the parallel running strips of film carrier tapes,
   a centrally located adjacent part guide portion positioned intermediate the side guide portions to guide adjacent innermost adjacent sides of the parallel running strips of film carrier tapes,
   said guide member further having undercut portions defining underlying spaces beneath each transverse region between each of the outermost side guide portions and the centrally located adjacent part guide portion whereby only edge portions of the adjacent strips are engaged by the guide member and the underlying spaces do not contact a central region of the strips running parallel through the guide member, whereby interaction between the edge support provided by the guide member and the drive gear and the back tension roller eliminates a transverse curling of the strips and causes the strips of film carrier tapes to reside in a common plane so as to locate an entire transverse width of the strips in a common focal length for simultaneous viewing of the strips in the inspecting station.

2. The apparatus for inspecting a film carrier tape for mounting electronic component according to claim 1, wherein separate dancer rollers are provided for the film carrier tapes for mounting electronic component, which are cut into strips, between the take-up device and the inspecting section, respectively.

3. The apparatus for inspecting a film carrier tape for mounting electronic component according to claim 1, wherein an identical dancer roller is provided for the film carrier tapes for mounting electronic component, which are cut into strips, between the take-up device and the inspecting section.

4. The apparatus for inspecting a film carrier tape for mounting electronic component according to claim 1, wherein the drive gear includes:
   a both end gear mated with a sprocket hole in side portions on both ends of the film carrier tape for mounting electronic component on the outermost side; and
   an intermediate gear mated with a sprocket hole provided in the adjacent side portions of the film carrier tape for mounting electronic component cut into strips between the both end gears.

5. An apparatus for inspecting a film carrier tape for mounting electronic component in which a plurality of electronic component mounting portions is provided in multiple strips in a transverse direction, comprising:
   an unwinding device for unwinding the film carrier tape for mounting electronic component in the multiple strips in which the individual film carrier tapes for mounting electronic component previously cut into strips are wound upon an unwinding reel, respectively;
   a back tension roller;
   an inspecting section for simultaneously inspecting the film carrier tapes for mounting electronic component, which are cut into strips, while causing them to run in parallel with each other;
   a drive gear;
   a take-up device for simultaneously taking up the film carrier tapes for mounting electronic component cut into strips, which are inspected in the inspecting section, upon a plurality of take-up reels attached to separate take-up shafts in parallel, respectively; and
   wherein the apparatus further comprises a guide member located at the inspection section for causing the cut strips of film carrier tapes to run in parallel with each other, the guide member comprising:
   a side guide portion formed on opposed transverse ends of the guide member to guide opposed outermost sides of the parallel running strips of film carrier tapes,
   a centrally located adjacent part guide portion positioned intermediate the side guide portions to guide adjacent innermost adjacent sides of the parallel running strips of film carrier tapes,
   said guide member further having undercut portions defining underlying spaces beneath each transverse region between each of the outermost side guide portions and the centrally located adjacent part guide portion whereby only edge portions of the adjacent strips are engaged by the guide member and the underlying spaces do not contact a central region of the strips running parallel through the guide member, whereby interaction between the edge support provided by the guide member and the drive gear and the back tension roller eliminates a transverse curling of the strips and causes the strips of film carrier tapes to reside in a common plane so as to locate an entire transverse width of the strips in a common focal length for simultaneous viewing of the strips in the inspecting station.

6. The apparatus for inspecting a film carrier tape for mounting electronic component according to claim 5, wherein the separate take-up shafts of the take-up device are constituted by an air shaft capable of expanding to increase a diameter thereof upon receipt of supply of air, and
   a plurality of take-up reels attached to the take-up shaft in parallel with each other is thus fixed, respectively.

7. The apparatus for inspecting a film carrier tape for mounting electronic component according to claim 5, wherein the drive gear includes:
   a both end gear mated with a sprocket hole in side portions on both ends of the film carrier tape for mounting electronic component on the outermost side; and
   an intermediate gear mated with a sprocket hole provided in the adjacent side portions of the film carrier tape for mounting electronic component cut into strips between the both end gears.

8. An apparatus for inspecting a film carrier tape for mounting electronic component in which a plurality of electronic component mounting portions is provided in multiple strips in a transverse direction, comprising:
   an unwinding device for unwinding the film carrier tape for mounting electronic component in the multiple strips which are wound upon an unwinding reel;
   a slit device for cutting the film carrier tapes for mounting electronic component in the multiple strips, which are unwound from the unwinding device, into individual film carrier tapes for mounting electronic component in strips;
   a back tension roller;
   an inspecting section for causing the film carrier tapes for mounting electronic component, which are cut into strips by the slit device, to run in parallel with each other and simultaneously inspecting them;
   a drive gear;
   a take-up device for simultaneously taking up the film carrier tapes for mounting electronic component cut into strips, which are inspected in the inspecting section, upon a plurality of take-up reels attached to an identical take-up shaft in parallel, respectively; and
   wherein the apparatus further comprises a guide member located at the inspection section for causing the cut strips of film carrier tapes to run in parallel with each other, the guide member comprising:
   a side guide portion formed on opposed transverse ends of the guide member to guide opposed outermost sides of the parallel running strips of film carrier tapes,
   a centrally located adjacent part guide portion positioned intermediate the side guide portions to guide adjacent innermost adjacent sides of the parallel running strips of film carrier tapes,
   said guide member further having undercut portions defining underlying spaces beneath each transverse region between each of the outermost side guide portions and the centrally located adjacent part guide portion whereby only edge portions of the adjacent strips are engaged by the guide member and the underlying spaces do not contact a central region of the strips running parallel through the guide member, whereby interaction between the edge support provided by the guide member and the drive gear and the back tension roller eliminates a transverse curling of the strips and causes the strips of film carrier tapes to reside in a common plane so as to locate an entire transverse width of the strips in a common focal length for simultaneous viewing of the strips in the inspecting station.

9. An apparatus for inspecting a film carrier tape for mounting electronic component in which a plurality of electronic component mounting portions is provided in multiple strips in a transverse direction, comprising:
   an unwinding device for unwinding the film carrier tape for mounting electronic component in the multiple strips which are wound upon an unwinding reel;

a slit device for cutting the film carrier tapes for mounting electronic component in multiple strips, which are unwound from the unwinding device, into individual film carrier tapes for mounting electronic component in strips;

a back tension roller;

an inspecting section for causing the film carrier tapes for mounting electronic component, which are cut into strips by the slit device, to run in parallel with each other and simultaneously inspecting them;

a drive gear;

a take-up device for simultaneously taking up the film carrier tapes for mounting electronic component cut into strips, which are inspected in the inspecting section, upon a plurality of take-up reels attached to separate take-up shafts in parallel, respectively; and wherein the apparatus further comprises a guide member located at the inspection section for causing the cut strips of film carrier tapes to run in parallel with each other, the guide member comprising:

a side guide portion formed on opposed transverse ends of the guide member to guide opposed outermost sides of the parallel running strips of film carrier tapes, a centrally located adjacent part guide portion positioned intermediate the side guide portions to guide adjacent innermost adjacent sides of the parallel running strips of film carrier tapes, said guide member further having undercut portions defining underlying spaces beneath each transverse region between each of the outermost side guide portions and the centrally located adjacent part guide portion whereby only edge portions of the adjacent strips are engaged by the guide member and the underlying spaces do not contact a central region of the strips running parallel through the guide member, whereby interaction between the edge support provided by the guide member and the drive gear and the back tension roller eliminates a transverse curling of the strips and causes the strips of film carrier tapes to reside in a common plane so as to locate an entire transverse width of the strips in a common focal length for simultaneous viewing of the strips in the inspecting station.

10. The apparatus for inspecting a film carrier tape for mounting electronic component according to claim 9, wherein the drive gear includes:

a both end gear mated with a sprocket hole in side portions on both ends of the film carrier tape for mounting electronic component on the outermost side; and an intermediate gear mated with a sprocket hole provided in the adjacent side portions of the film carrier tape for mounting electronic component cut into strips between the both end gears.

11. The apparatus for inspecting a film carrier tape for mounting electronic component according to claim 10, further comprising a guide roller, the guide roller including:

a side guide protruded portion on both ends which serves to guide both end side portions of the film carrier tape for mounting electronic component on the outermost side; and an adjacent part guide protruded portion protruded to separate and guide adjacent side portions of the film carrier tapes for mounting electronic component cut into strips between the side guide protruded portions on the both ends.

12. The apparatus for inspecting a film carrier tape for mounting electronic component according to claim 9, wherein a plurality of take-up reels, which are attached to the identical take-up shaft of the take-up device in parallel with each other, are fixed into through holes provided in the vicinity of centers of the reels by means of removable engaging bar members.

13. The apparatus for inspecting a film carrier tape for mounting electronic component according to claim 9, wherein the plurality of take-up reels, which are attached to the separate take-up shafts of the take-up device in parallel with each other, are fixed into through holes provided in the vicinity of centers of the reels by means of removable engaging bar members, respectively.

14. The apparatus for inspecting a film carrier tape for mounting electronic component according to claim 9, wherein the identical take-up shaft of the take-up device is constituted by an air shaft capable of expanding to increase a diameter thereof upon receipt of supply of air, and a plurality of take-up reels attached to the take-up shaft in parallel with each other is thus fixed to each other.

15. The apparatus for inspecting a film carrier tape for mounting electronic component according to claim 9, wherein the inspecting section includes a magnifying lens device for magnifying the film carrier tape for mounting electronic component in order to carry out an inspection, the magnifying lens device including a magnifying lens for magnifying, in a total width direction, the film carrier tapes for mounting electronic component, which are cut into strips and running in parallel with each other.

16. The apparatus for inspecting a film carrier tape for mounting electronic component according to claim 15, wherein the magnifying lens device has a magnification of 1.4 or more at an enlargement ratio of a length.

17. The apparatus for inspecting a film carrier tape for mounting electronic component according to claim 9, wherein separate dancer rollers are provided for the film carrier tapes for mounting electronic component, which are cut into strips, between the unwinding device and the inspecting section, respectively.

18. The apparatus for inspecting a film carrier tape for mounting electronic component according to claim 17, further comprising a looseness control device for detecting a position of the dancer roller to control an amount of looseness of the film carrier tape for mounting electronic component.

19. The apparatus for inspecting a film carrier tape for mounting electronic component according to claim 18, wherein the looseness control device includes a guide member for separately changing a guide path for the film carrier tape for mounting electronic component in each strip which is to be guided by the dancer roller.

20. The apparatus for inspecting a film carrier tape for mounting electronic component according to claim 9, wherein an identical dancer roller is provided for the film carrier tapes for mounting electronic component, which are cut into strips, between the unwinding device and the inspecting section.

* * * * *

UNITED STATES PATENT AND TRADEMARK OFFICE
CERTIFICATE OF CORRECTION

| | | |
|---|---|---|
| PATENT NO. | : 7,219,708 B2 | Page 1 of 1 |
| APPLICATION NO. | : 10/783114 | |
| DATED | : May 22, 2007 | |
| INVENTOR(S) | : Yamamoto et al. | |

It is certified that error appears in the above-identified patent and that said Letters Patent is hereby corrected as shown below:

<u>Title page,</u> Item (57) ABSTRACT, line 14, "in stripes strips" should read -- in strips --

Signed and Sealed this

Thirteenth Day of November, 2007

JON W. DUDAS
*Director of the United States Patent and Trademark Office*